United States Patent
van Sparrentak et al.

(10) Patent No.: US 10,039,553 B2
(45) Date of Patent: Aug. 7, 2018

(54) CLAMPING DEVICE FOR REDUCING VENOUS BLOOD FLOW

(71) Applicant: Tournicare Pty Ltd, Camberwell, Victoria (AU)

(72) Inventors: Niels van Sparrentak, Balwyn (AU); Rohan White, Hawthorn (AU)

(73) Assignee: Tournicare Pty Ltd, Camberwell, Victoria (AU)

( * ) Notice: Subject to any disclaimer, the term of this patent is extended or adjusted under 35 U.S.C. 154(b) by 246 days.

(21) Appl. No.: 14/888,641

(22) PCT Filed: May 7, 2014

(86) PCT No.: PCT/AU2014/000499
§ 371 (c)(1),
(2) Date: Nov. 2, 2015

(87) PCT Pub. No.: WO2014/179830
PCT Pub. Date: Nov. 13, 2014

(65) Prior Publication Data
US 2016/0066925 A1    Mar. 10, 2016

(30) Foreign Application Priority Data

May 7, 2013  (AU) ............................... 2013901617
Jul. 16, 2013  (AU) ............................... 2013902638

(51) Int. Cl.
*A61B 17/00*    (2006.01)
*A61B 17/132*    (2006.01)
(Continued)

(52) U.S. Cl.
CPC .......... *A61B 17/132* (2013.01); *A61B 17/135* (2013.01); *A61B 17/1355* (2013.01); *A61B 2017/12004* (2013.01)

(58) Field of Classification Search
CPC . A61B 17/132; A61B 17/1327; A61B 17/135; A61B 2017/12004
See application file for complete search history.

(56) References Cited

U.S. PATENT DOCUMENTS 3,884,240 A     5/1975  Gilman
2003/0055453 A1*  3/2003  Akerfeldt ............. A61B 17/135
                                                              606/203

(Continued)

FOREIGN PATENT DOCUMENTS

WO     WO2011059429 A1    5/2011
WO     WO2014017975 A1    1/2014
WO     WO2014191987 A1    12/2014

OTHER PUBLICATIONS

Kharbanda et al., Transient Limb Ischemia Induces Remote Ischemic Preconditioning in Vivo, Circulation, 2002:106, pp. 2881-2883.

(Continued)

*Primary Examiner* — Ashley Fishback
(74) *Attorney, Agent, or Firm* — Bret E. Field; Bozicevic, Field & Francis LLP

(57) ABSTRACT

Some embodiments relate to a device for reducing venous blood flow in a human limb. The device of some embodiments comprises: a first rigid part having a first non-linear inner profile; a second rigid part having a second inner profile generally facing the first inner profile; and a coupling portion that couples the first and second parts together while allowing relative movement of the first and second parts between a clamped position and an unclamped position. The first and second inner profiles are arranged to press against veins in the limb when the device is in the clamped position and thereby reduce venous blood flow in the limb.

23 Claims, 28 Drawing Sheets

(51) Int. Cl.
*A61B 17/135* (2006.01)
*A61B 17/12* (2006.01)

(56) References Cited

U.S. PATENT DOCUMENTS

| | | | |
|---|---|---|---|
| 2008/0077151 A1* | 3/2008 | Kring | A61B 17/132 |
| | | | 606/88 |
| 2008/0146947 A1* | 6/2008 | Kojima | A61B 5/0002 |
| | | | 600/490 |
| 2011/0040196 A1 | 2/2011 | Shih et al. | |
| 2012/0004559 A1 | 1/2012 | Lee et al. | |
| 2014/0114117 A1 | 4/2014 | Naghavi et al. | |

OTHER PUBLICATIONS

Cushman et al. Laboratory Methods and Quality Assurance in the Cardiovascular Health Study, Clinical Chemistry, vol. 41, No. 2, 1995, pp. 264-270.

\* cited by examiner

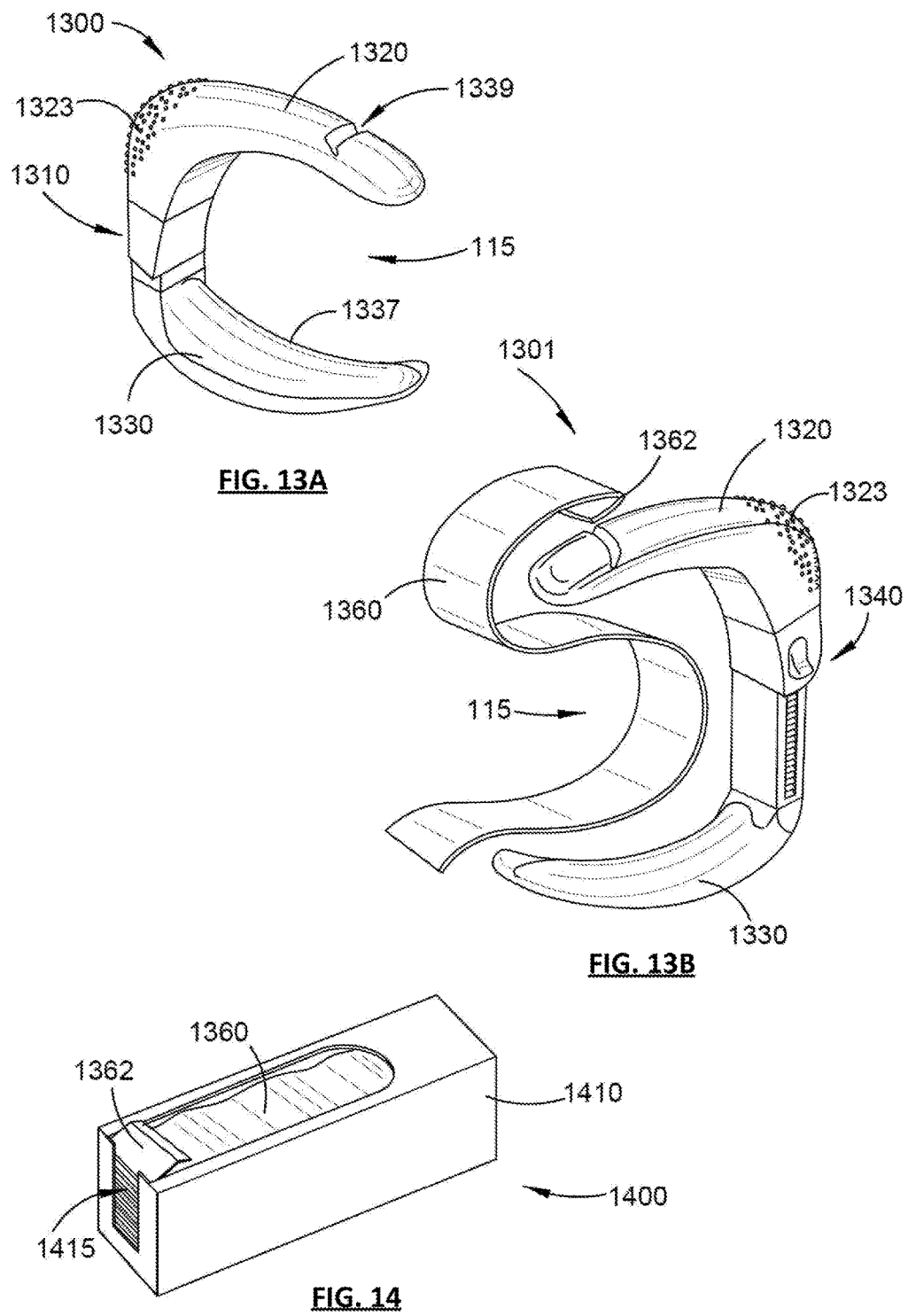

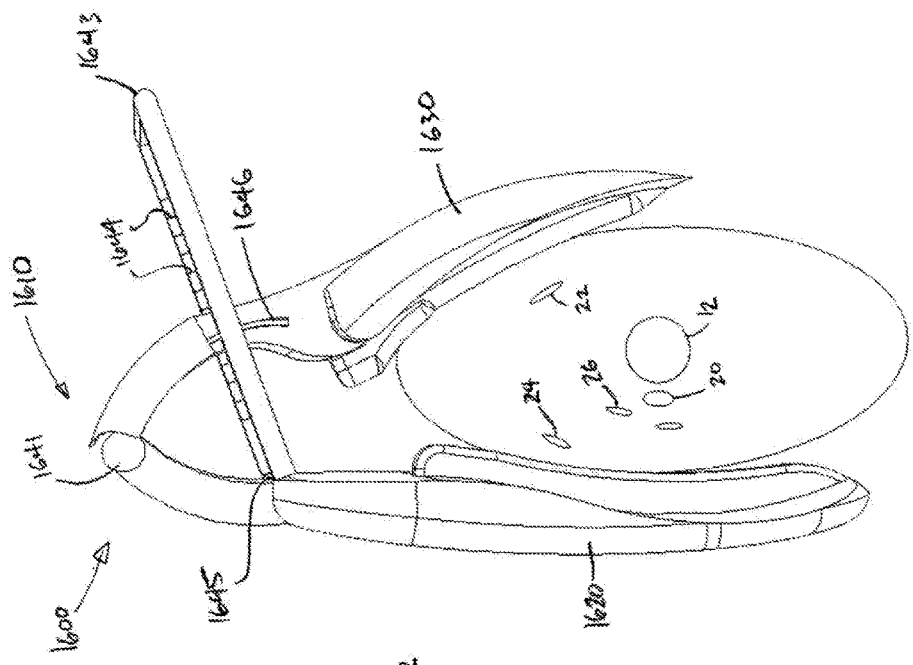
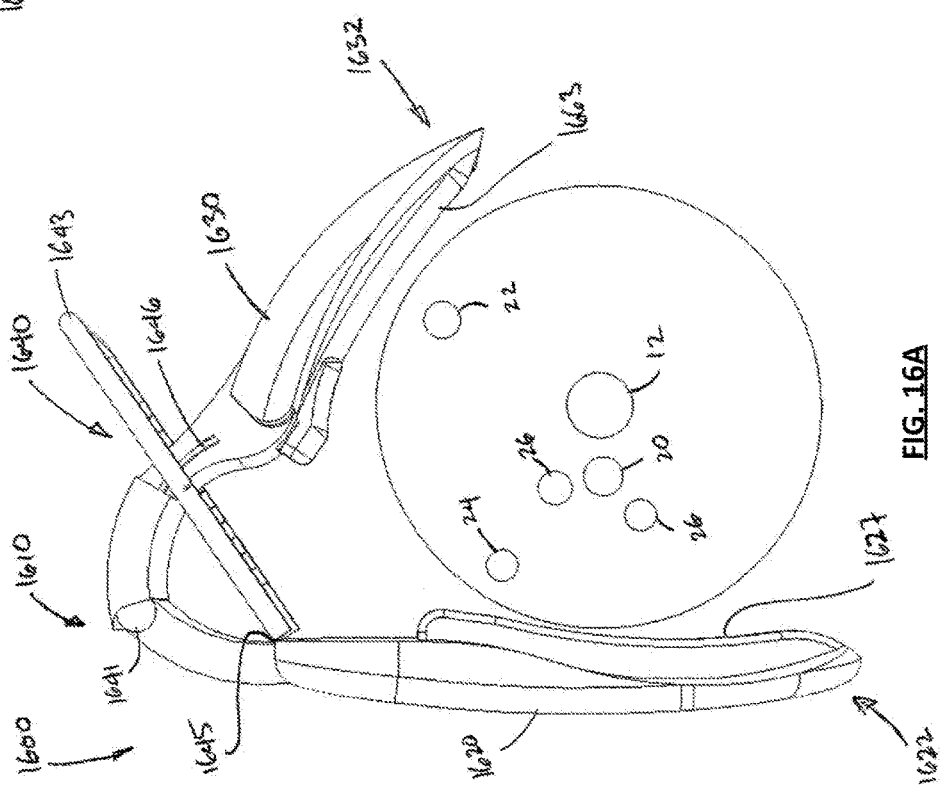

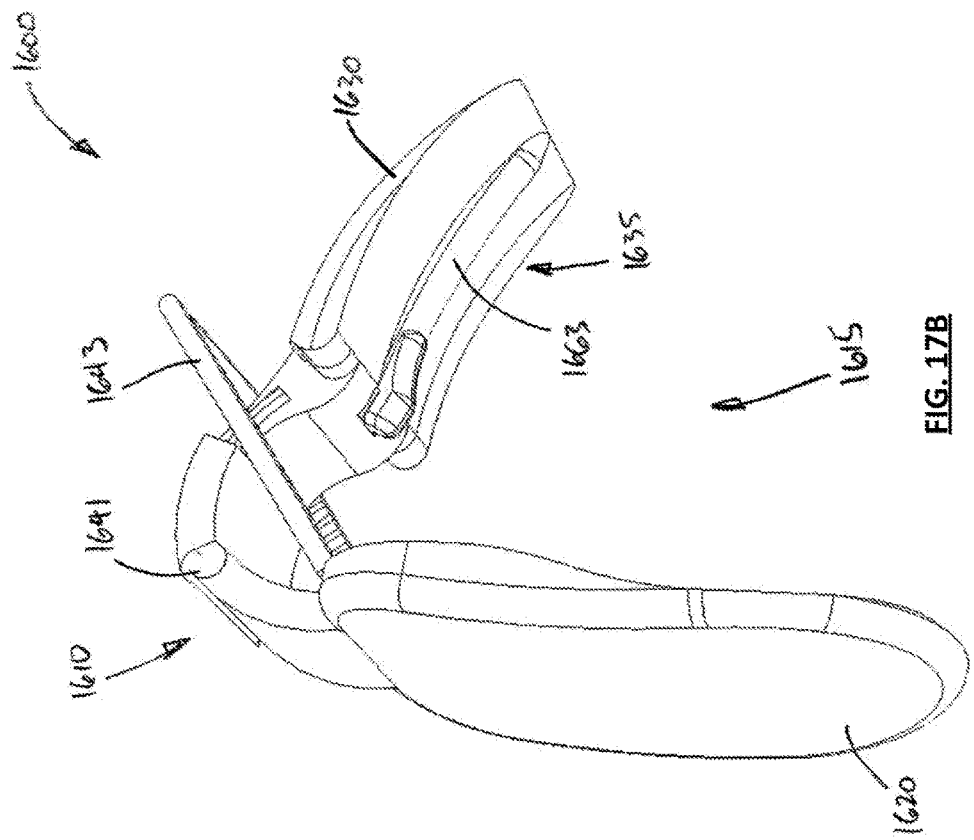
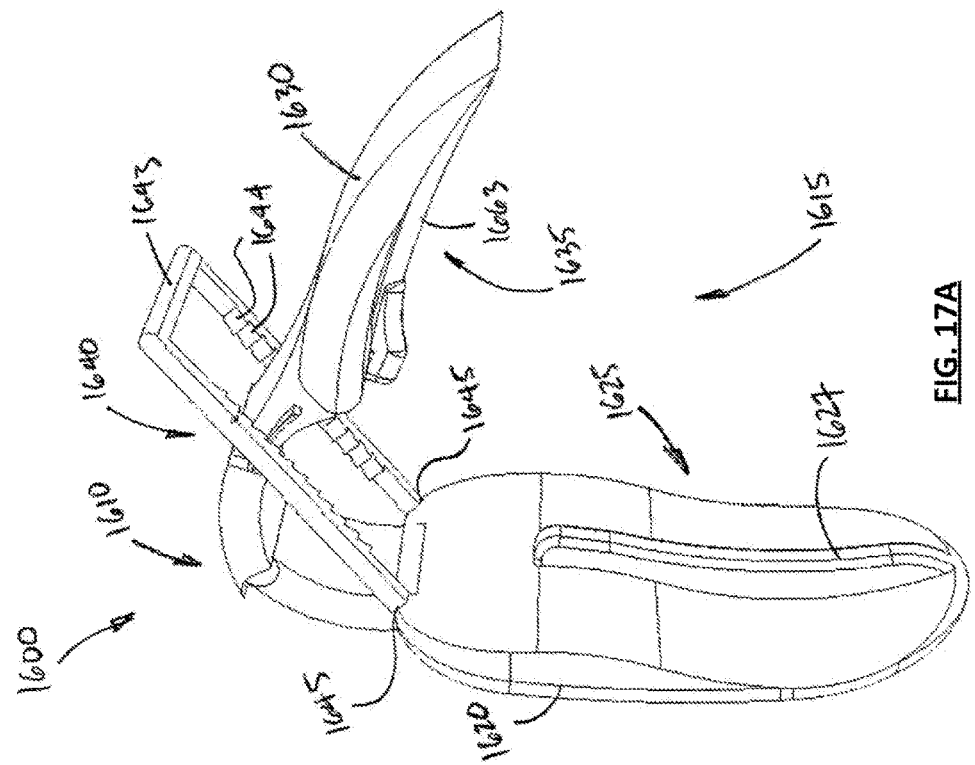
FIG. 17A
FIG. 17B

CLAMPING DEVICE FOR REDUCING VENOUS BLOOD FLOW

TECHNICAL FIELD

Described embodiments generally relate to clamping devices for reducing venous blood flow. In particular, embodiments relate to clamping devices with opposed parts that are movable between a clamped position and an unclamped position about a limb.

BACKGROUND ART

Tourniquets have been used traditionally for many years when performing venepuncture. Such tourniquets generally consist of a flexible band to encircle the arm or lower limb and compress the arm or lower limb around the circumference of that limb. It has been common practice to use such tourniquets repeatedly for multiple patients. In some circumstances, blood or other bodily fluids may splatter onto the tourniquet and the tourniquet may pick up and harbour bacteria from the skin during repeated use. Such repeated use of traditional tourniquets is therefore unhygienic and involves a risk of communication of disease.

Additionally, traditional tourniquets require the use of two hands to apply them, which can be awkward if the medical practitioner is therefore unable to perform another desired function simultaneously. Some traditional tourniquets may, when released, experience a somewhat violent and sudden release, which can be irksome for the patient or medical practitioner releasing the tourniquet. Further, some traditional tourniquets may tend to pinch the skin of the patient when applying compression to the limb, causing pain and discomfort. Further, traditional tourniquets do not allow a medical practitioner to tell how much pressure is being applied. If the tourniquet is applied too tightly or too loosely, it can negatively affect the distension of veins in the limb around which the tourniquet is applied, which in turn can negatively affect patient outcomes.

It is desired to address or ameliorate one or more shortcomings of disadvantages associated with prior methods or devices for reducing venous blood flow in a limb or to at least provide a useful alternative thereto.

SUMMARY

Some embodiments relate to a device for reducing venous blood flow in a human limb, the device comprising:
a first rigid part having a first non-linear inner profile;
a second rigid part having a second inner profile generally facing the first inner profile; and
a coupling portion that couples the first and second parts together while allowing relative movement of the first and second parts between a clamped position and an unclamped position;
wherein the first and second inner profiles are arranged to press against veins in the limb when the device is in the clamped position and thereby reduce venous blood flow in the limb.

The first and second inner profiles may define clamping surfaces to press against veins in the limb when the device is in the clamped position. The first inner profile may be curved or may be partly curved and partly straight or may have parts of different curvatures. The second inner profile may be non-linear. The second inner profile may be curved or may be partly curved and partly straight or may have parts of different curvatures.

The coupling portion may comprise a first coupling portion and a second coupling portion that is movable relative to the first coupling portion to allow the device to adopt the clamped position or the unclamped position. The first coupling portion may be connected to the first rigid part and the second coupling portion may be connected to the second rigid part.

The device may further comprise at least one releasable retention mechanism to retain the device in the clamped position. The at least one retention mechanism may be configured to allow the device to adopt one of a plurality of retention positions in which the coupling portion is restrained from adopting the unclamped position. The plurality of retention positions may comprise a plurality of discrete retention positions. The at least one retention mechanism may comprise a ratcheting retention mechanism. The at least one retention mechanism may comprise a plurality of separate retention components. The retention mechanism may comprise a frictional engagement mechanism.

The device may further comprise, for each at least one retention mechanism, a manually actuable release mechanism to release the device from the clamped position.

The device may further comprise a ridge projecting from at least one of the first inner profile and the second inner profile, the ridge being sized to press inwardly on the limb when the device is in the clamped position. The ridge may extend along a substantial part of the first inner profile and/or the second inner profile. The ridge may have a curved cross-sectional profile resembling a bead.

The device may further comprise a biasing mechanism to bias the device toward the unclamped position. The biasing mechanism may be disposed in or on the coupling portion. The second part may be partially received within a receiving portion of the first part. As the device is moved toward the clamped position, progressively more of the second part may be received within the receiving portion of the first part.

The first and second rigid parts may be sized and shaped so that, when the device is positioned on the arm and is in the clamped position, the device cannot be easily removed from the upper arm. The first and second rigid parts may be sized and shaped so that, when the device is in the unclamped position, the device can be easily put on the upper arm or removed from the upper arm.

The first and second rigid parts may be sized and shaped so that, when the device is in the clamped position, the first and second rigid parts do not necessarily contact the entire periphery/circumference of the limb. The first and second rigid parts may be sized and shaped to provide only partial encirclement of the limb when the device is in the clamped position. The first and second rigid parts may be sized and shaped to provide partial encirclement of the limb in a range of about 240° to about 300° when the device is in the clamped position.

The device may be sized and shaped so that it can be manually placed over the upper arm in the unclamped position using only one hand and moved into the clamped position using only one hand. The device may be sized and shaped so that it can be manually released from the clamped position using only one hand and removed from the limb using only one hand.

The device may further comprise a cushioning element disposed on at least one of the first inner profile and the second inner profile. The cushioning element may extend over the first inner profile and the second inner profile. The cushioning element may be affixed to the first inner profile and is not affixed to the second inner profile.

When relative movement occurs between the first and second parts, relative movement may be permitted between the cushioning element and the second inner profile. The second part may define an aperture to receive a part of the cushioning element so that, when relative movement occurs between the first and second parts, the part of the cushioning element is permitted to move through the aperture. The aperture may extend through the second part from the second inner profile to an external wall of the second part, whereby the part of the cushioning element can extend through the second part from one side to another side. Alternatively, the second part may define a chamber to progressively receive the part of the cushioning element as relative movement occurs between the first part and the second part towards the clamped position.

The device may further comprise a ridge defined by at least one of the cushioning element and the second inner profile, the ridge extending along at least part of a length of the cushioning element and arranged to impinge on the limb when the device is in the clamped position. The ridge may extend centrally along a longitudinal length of the cushioning element. The cushioning element may comprise a flexible backing layer and a compressible cushioning layer affixed to the backing layer. The first and second parts may be coupled by the coupling portion so that relative movement between the first and second parts is only permitted in a plane in which the first part, the second part and the coupling portion co-extend. In some embodiments, relative movement may only be permitted along a single axis in the plane. In other embodiments, relative movement may be permitted in more than one direction in the plane.

The first part, the second part and the coupling portion may be formed of one or more sterilisable materials.

The first part, the second part and the coupling portion may define a shape of the device that is substantially U-shaped. The first part may have a free end and a first distal portion at the free end of the first part that is distal from the coupling portion and the second part may have a free end and a second distal portion at the free end of the second part that is distal from the coupling portion, wherein in the unclamped position, a gap may be defined between the first and second distal portions that is sized to allow the device to be placed over the upper arm so that the upper arm is received in a space defined between the first and second parts. When the first and second parts are moved to the clamped position, the gap may be reduced or eliminated.

At least one of the first and second distal portions may curve inward toward the other of the first and second distal portions. At least one of the first and second inner profiles may be generally concave.

The coupling portion or the first and second parts or jaws may define (or may have parts or projections that define) oppositely facing lands that can be manually pressed toward each other to move the first part and the second part into the clamped position from the unclamped position.

Some embodiments relate to a device for reducing venous blood flow, the device comprising:
  first and second opposed jaws, each of the first and second
    jaws defining a rigid inner face to be pressed toward
    opposite sides of a limb and the jaws together defining
    a space therebetween to at least partially receive the
    limb, the inner face of at least one of the first and
    second jaws having a non-linear profile;
  a bridge coupling the first and second jaws together in a
    manner that allows relative movement of the first and
    second jaws between an open position, in which the
    device can be positioned about at least a portion of the
    limb, and a clamped position, in which the inner faces
    of the first and second jaws are pressed against the
    opposite sides of the limb such that venous blood flow
    is reduced in at least superficial veins distal of the
    portion of the limb.

Some embodiments relate to a device for reducing venous blood flow in a limb, the device comprising:
  first and second opposed jaws, each of the first and second
    jaws comprising a rigid component defining an inner
    face to be pressed toward opposite sides of the limb;
  wherein the first and second jaws are movable between an
    open position, in which the device can be positioned
    about at least a portion of the limb, and a clamped
    position, in which the inner faces of the first and second
    jaws are pressed against the opposite sides of the limb
    such that venous blood flow is reduced in at least
    superficial veins distal of the portion of the limb;
  wherein the jaws are manually compressible from the
    open position to the clamped position; and
  wherein the device is sized and arranged such that, when
    the limb is an upper arm and the device is placed in the
    clamped position about the upper arm with one of the
    first and second jaws pressing against a medial side of
    the upper arm, the other of the first and second jaws
    presses against an upper lateral part of the upper arm to
    compress the cephalic vein.

In some embodiments, the device may further comprise at least one pressure sensor. The at least one pressure sensor may be positioned on or adjacent at least one of the first rigid part and the second rigid part or at least one of the first and second jaws. The at least one pressure sensor may be positioned in the device so that, in use of the device on arm, the at least one pressure sensor lies adjacent a medial part of the arm.

The device may further comprise an indicator coupled to the at least one pressure sensor to visibly indicate a sensed pressure. The at least one pressure sensor may further comprise a piezoelectric element.

The device may further comprise an expandable element arranged at least partly along at least one of the first inner profile and the second inner profile or at least one of the inner faces of the first and second jaws. The expandable element may be inflatable to apply pressure to the limb when the device is positioned on the limb. The expandable element may have a valve to selectively allow passage of air into or out of the expandable element. The expandable element may form part of or may be at least partially enclosed by a cushioning element disposed along at least one of the first and second inner profiles or at least one of the inner faces of the first and second jaws. The at least one pressure sensor may be arranged to sense a pressure applied at least in part by the expandable element.

Some embodiments may further comprise a pump to inflate the expandable element. The pump may be disposed inside one of the first part and the second part. The device may further comprise a controller arranged to operate the pump and a power source to power the controller and the pump.

The device may further comprise one or more manually actuable input components on an outside of one of the first part and the second part to provide actuation input to the controller. The controller may be configured to, in response to the actuation input, one of:
  operate the pump to inflate the expandable element to a
    first pressure set-point;

operate the pump to inflate the expandable element to a second pressure set-point that is higher than the first pressure set-point;

operate a pressure relief valve to deflate the expandable element; and stop operation of the pressure relief valve.

The first pressure set-point may be a pressure from about 40 mm Hg to about 80 mm Hg, optionally about 60-70 mm Hg. The second pressure set-point may be a pressure from about 80 mm Hg to about 200 mm Hg, optionally about 90-100 mm Hg.

The device may further comprise an audio input component. The controller may be configured to process speech signals received via the audio input component and to determine whether a valid voice command has been received and, if a valid voice command is determined to have been received, to operate the pump or a pressure relief valve in response to the valid voice command.

The device may further comprise a wireless communication module. The controller may be configured to receive a control command from an external control device via the wireless communications module and to operate the pump or a pressure relief valve in response to the control command.

The device may be configured so that sufficient force can be applied to the limb by the device in the clamped position to cause at least partial arterial occlusion in the limb.

Some embodiments relate to a kit comprising the device as described above and further comprising a cradle to receive and support the device in the unclamped position.

Some embodiments relate to a kit comprising the device described above and further comprising a thin, optionally disposable, cover or liner that is configured to at least cover and hygienically protect parts of the device that are likely to come into contact with the limb when the device is in the clamped position on the limb. The cover or liner may be pre-packaged as a clean and sterilised item ready for use.

The disposable cover may be configured to cover most or all of the first and second parts. The disposable cover may define first and second pockets to receive and substantially surround the first and second parts or jaws of the device. Alternatively, the disposable cover may be configured to substantially cover the first and second inner profiles.

BRIEF DESCRIPTION OF THE DRAWINGS

Embodiments are described in further detail below, by way of example, with reference to the accompanying drawings, in which:

FIG. 13A is a perspective schematic illustration of a clamping device according to some embodiments;

FIG. 13B is a perspective schematic illustration of a kit comprising a disposable clamp cover according to some embodiments and the clamping device of FIG. 13A;

FIG. 14 is a schematic illustration of a container housing disposable covers for use with the kit of FIG. 13B;

FIG. 16A is a schematic view illustrating a clamping device according to further embodiments, showing placement of the device about an uncompressed upper arm, with the device in the unclamped position;

FIG. 16B is a schematic illustration of the clamping device similar to FIG. 16A but shown in a clamped position, in which the upper arm is compressed;

FIG. 17A is a first perspective view of the clamping device of FIG. 16A, shown in an open position;

FIG. 17B is a second perspective view of the clamping device of FIG. 16A, shown in an open position;

DETAILED DESCRIPTION

Described embodiments generally relate to clamping devices for reducing venous blood flow. In particular, embodiments relate to clamping devices with opposed parts (jaws) that are movable between a clamped position and an unclamped position about a limb.

In contrast to a circumferential tourniquet design that envelopes the upper arm or other limb in total, the described and claimed clamping devices are closer to a clamp/brace-style design, optionally with pressure points where needed to compress the main veins in the upper arm or other limb. This clamp-style device design may advantageously reduce patient discomfort, injury risk and improve efficiency in application of compression as part of the venepuncture procedure. Additionally, the open U-shape of described embodiments allows a disposable liner to be easily applied to the device and removed for disposal to provide improved hygiene.

Figure 1A:
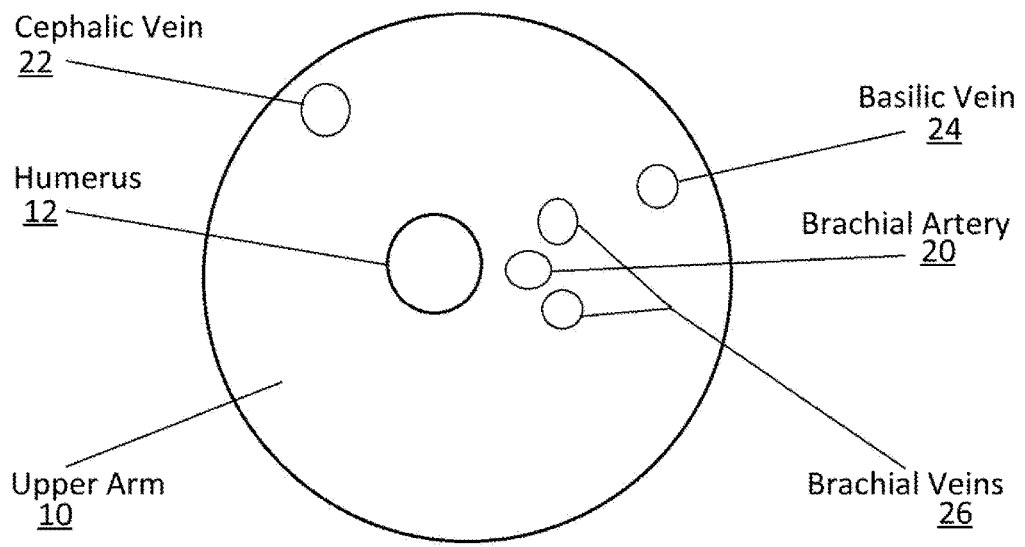
FIG. 1A is a rough anatomical cross-sectional view across an upper arm in an uncompressed state.
Figure 1B:
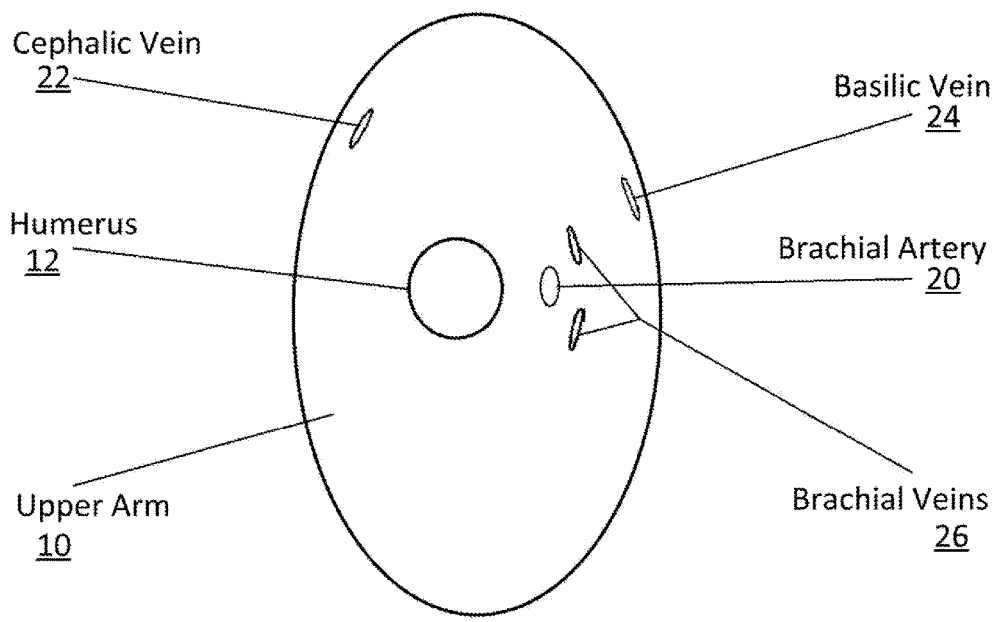
FIG. 1B is a rough anatomical cross-sectional view similar to FIG. 1A, showing the upper arm in a compressed state.

Referring firstly to FIGS. 1A and 1B, certain parts of the anatomy of the upper human arm are discussed for purposes of illustration of an intended use of the clamping device according to some embodiments.

A human upper arm 10 generally has a centrally positioned humerus bone 12 around which tissues are arranged including muscles, veins and arteries. A significant artery in the upper arm 10 is the brachial artery 20 which is generally located deeper within the flesh of the upper arm 10 than the veins, such as the cephalic vein 22, basilica vein 24 and brachial veins 26. FIG. 1A shows the upper arm in an uncompressed state 4a and FIG. 1B shows the upper arm 10 in a laterally and medially compressed state 4b.

As is roughly illustrated in FIG. 1B, in the compressed state 4b, the veins closer to the surface of the upper arm 10 tend to become more compressed when compression is applied to the external lateral and medial surfaces of the upper arm 10. This compression tends to reduce blood flow in the cephalic vein 22, basilic vein 24 and brachial veins 26, which tends to have the effect of reducing blood flow in those veins back to the heart. Since there is greater fluid pressure in the brachial artery 20 and it is positioned more deeply in the arm, there tends to be less choking of the blood flow through the brachial artery 20 as a result of inwardly applied compression to the exterior of the arm, when compared to venous blood flow under such compression. Generally, the cephalic vein is positioned on an upper lateral (outer) side of the arm, while the brachial and basilic veins are positioned on the medial (inner) side of the arm.

With reference to FIGS. 2A, 2B, 3A, 3B, 4A, 4B, 5A and 5B, a clamping device 100 according to some embodiments is shown and described in further detail. The clamping device 100 generally comprises a first rigid part 120 and a second rigid part 130 that are coupled by coupling or bridge portion 110. The first and second parts 120, 130 may be described as arms or jaws because of their opposed relation and their function of clamping about a limb. As is shown in the Figures, the device 100 is generally approximately U-shaped, with the coupling or bridge portion 110 joining the first and second jaws 120, 130 at an apex of the U-shape.

Device 100 (or another device embodiment described herein) is generally configured to be movable between an unclamped position, in which the jaws 120, 130 are spaced widely enough to allow the device 100 to be placed about or partially about a human limb, such as an upper arm, and a clamped position in which the jaws 120, 130 press toward and against the lateral and medial surfaces of the limb. While embodiments are generally described as being configured for clamping a human upper arm, embodiments may also be configured for clamping other limb parts such as a forearm, a lower leg or an upper leg, for example.

The device 100 is generally formed to have a rigid body 101 that is formed of two main movable parts, comprising the first and second jaws 120, 130. The coupling or bridge portion 110 comprises first and second coupling parts that are each coupled, connected to or integrally formed with the jaws 120, 130, such that relative movement of the first and second coupling parts when the device 100 transitions between the clamped and unclamped positions, corresponds with relative movement between the first and second jaws 120, 130.

The first jaw 120 has a base portion 121 that forms part of the coupling or bridge portion 110. The second jaw 130 also has a base portion 131 that forms part of the bridge or coupling portion 110. The first jaw 120 also has a distal portion 122 at a free end distal of the base portion 121. The first jaw 120 defines a generally non-linear inner profile 125 that faces an opposite non-linear inner profile 135 defined by the opposing second jaw 130.

On an outward face of the base portion 120, there is a land 123 and on an outward face of the base portion 131 of the second jaw 130, there is another land 133. The lands 123, 133 are generally arranged to be manually compressible by a human hand, such that a thumb can be placed on one of the lands 123, 133, while one or more fingers are placed on the opposite land 123, 133 so that manual force can be used to squeeze and move the jaws 120, 130 toward each other and thereby move the device 100 into a clamped position. In some embodiments, the lands 123, 133 may be arranged at opposite ends of the coupling portion 110. In other embodiments, the lands 123, 133 may be defined by oppositely directed faces of projections extending from respective parts 1230, 130.

Device 100 and other device embodiments described herein advantageously allow application of the device to the left or right arm. Where the inner profiles of the clamping two jaws are not symmetrical about the bridge portion, the device can be readily reversed in orientation to accommodate placement on either the left or right arm.

In order to maintain the device 100 in the clamped position, the device 100 has at least one retention mechanism 140. As shown in the Figures, a retention mechanism 140 may be disposed on opposite sides of the coupling or bridge portion 110. The one or more retention mechanisms 140 are configured to retain the device 100 in a compressed, clamped position once the jaws 120, 130 are moved toward each other. In particular, at least one retention mechanism 140 is configured to allow the device 100 to adopt one of a plurality of retention positions in which the coupling portion 110 is retrained from adopting an unclamped position.

Each retention mechanism 140 may be configured to adopt one of a plurality of discrete retention positions as the jaws 120, 130 are moved from an unclamped position to a clamped position. The specific discrete retention position adopted in the clamped position will depend on the size of the limb about which the device 100 is positioned as well as the degree of compressive force applied in manually driving the jaws 120, 130 toward each other.

Figures 2A, 2B:
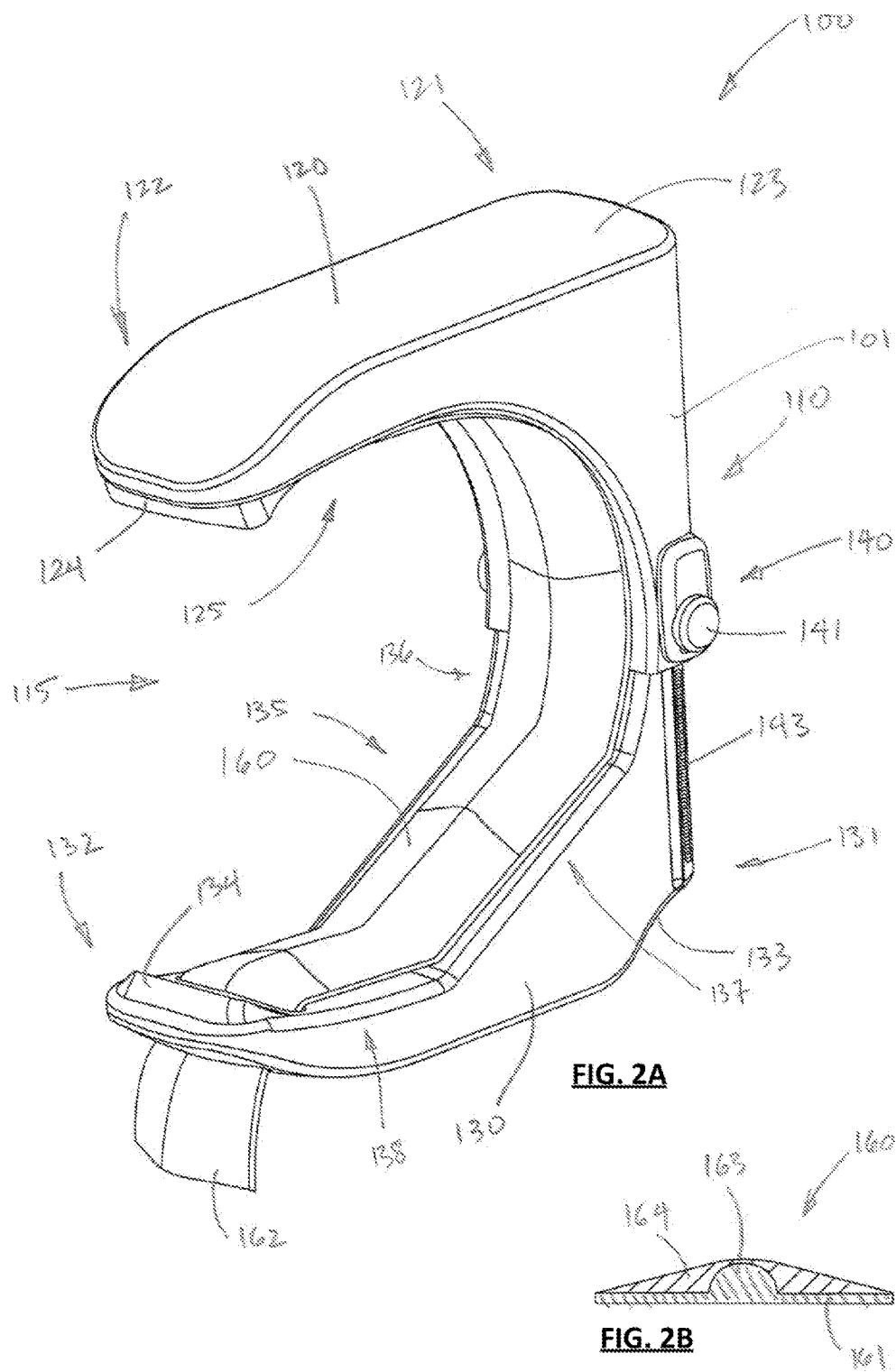
FIG. 2A is a perspective view of a clamping device according to some embodiments.
FIG. 2B is a cross-sectional view of a liner part of the device of FIG. 2A.
Figure 3A:
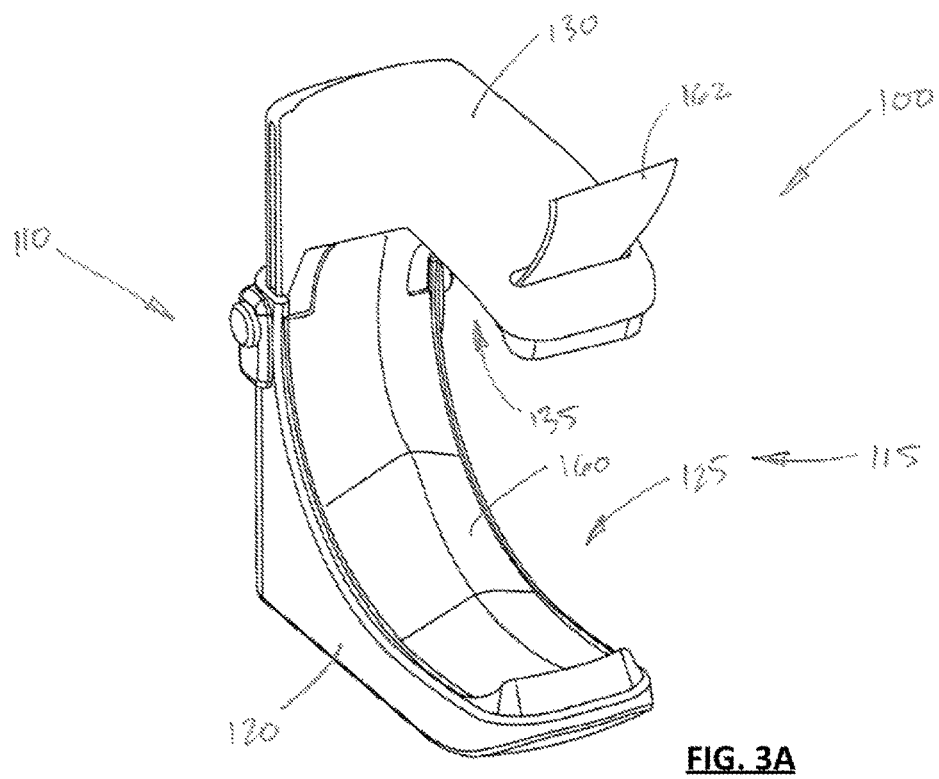
FIG. 3A is a perspective view of the device of FIG. 2A, shown from a different angle.
Figure 3B:
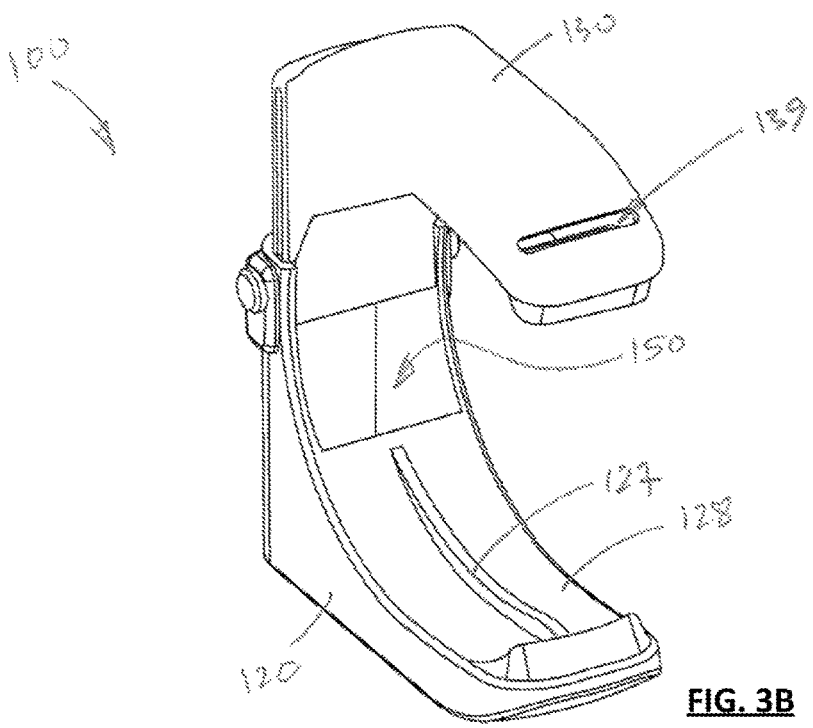
FIG. 3B is a perspective view of the device of FIG. 2A, shown from a perspective view similar to that of FIG. 3A, but with a cushioning liner absent.
Figure 4A:
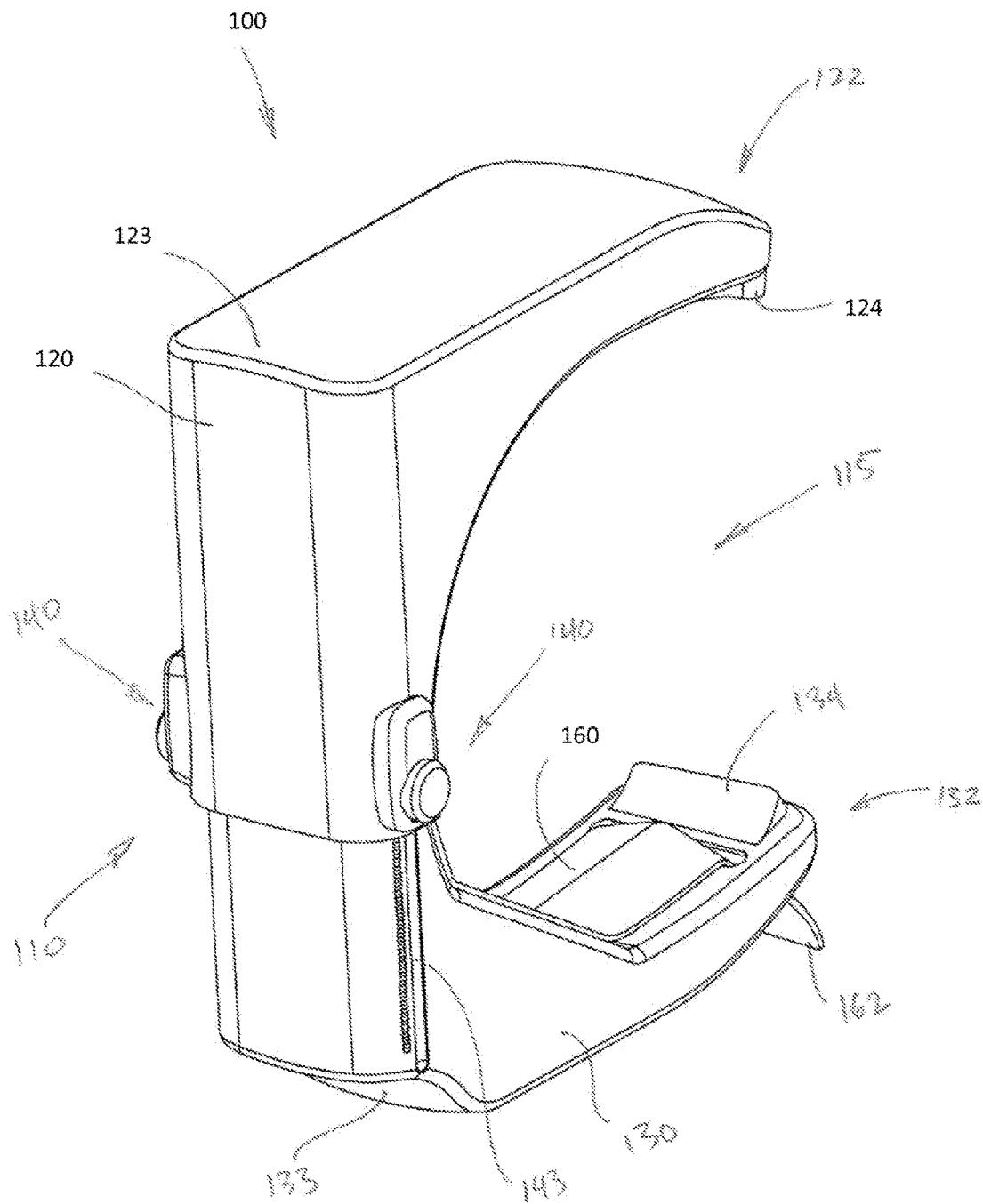
FIG. 4A is a further perspective view of the device of FIG. 2A, shown in an open or unclamped position.
Figure 4B:
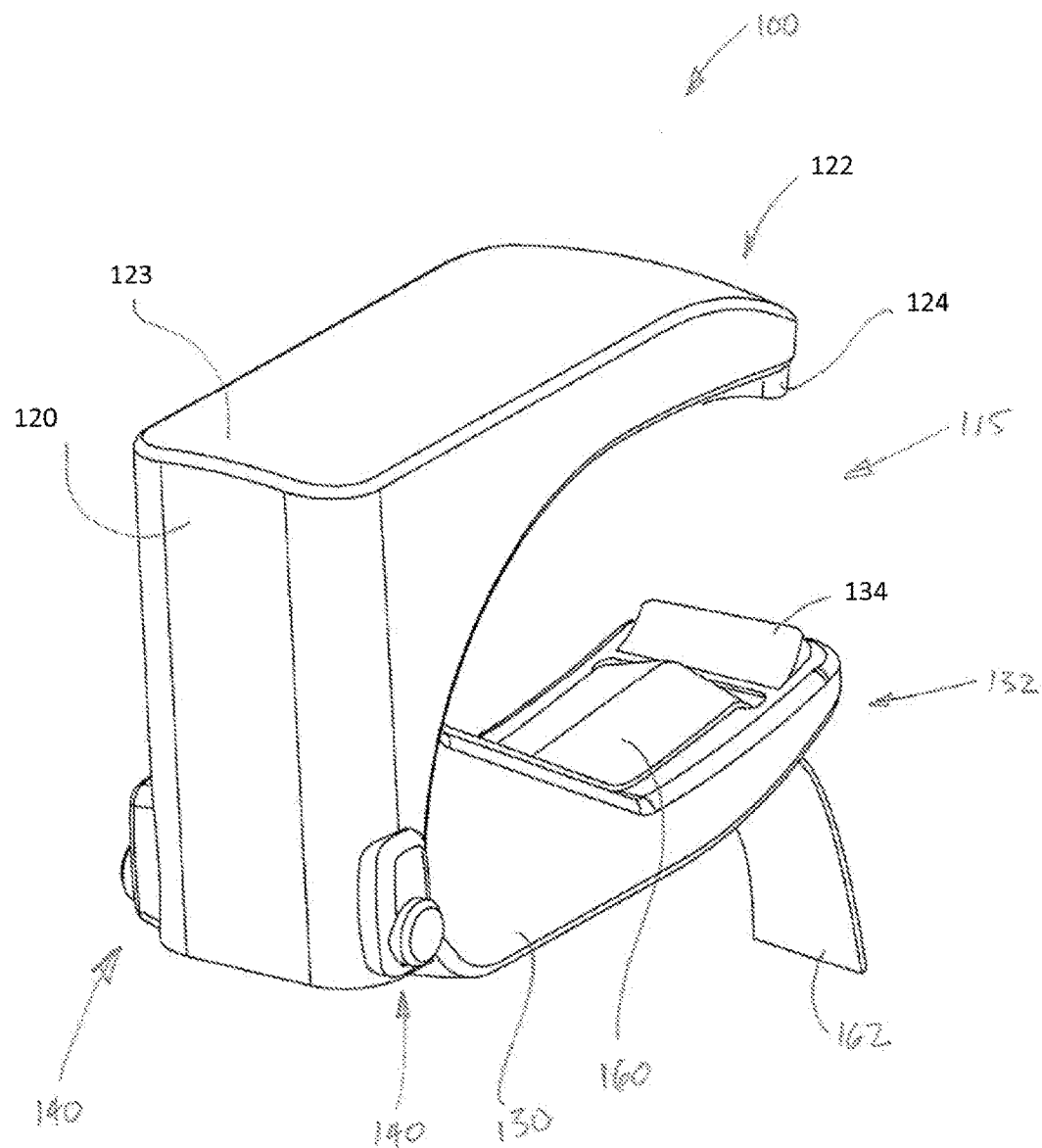
FIG. 4B is a view of the device similar to that shown in FIG. 4A but shown in a compressed or clamped position.
Figure 5A:
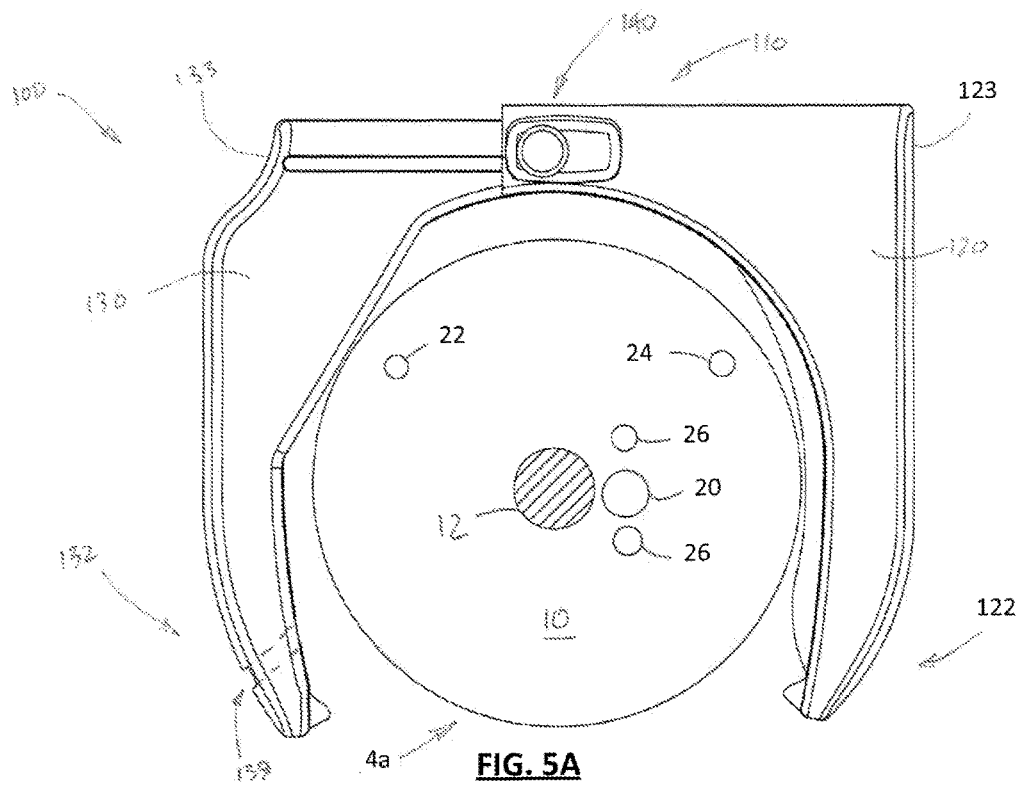
FIG. 5A is a schematic view illustrating placement of the device of FIG. 2A about an uncompressed upper arm, with the device in the unclamped position.
Figure 5B:
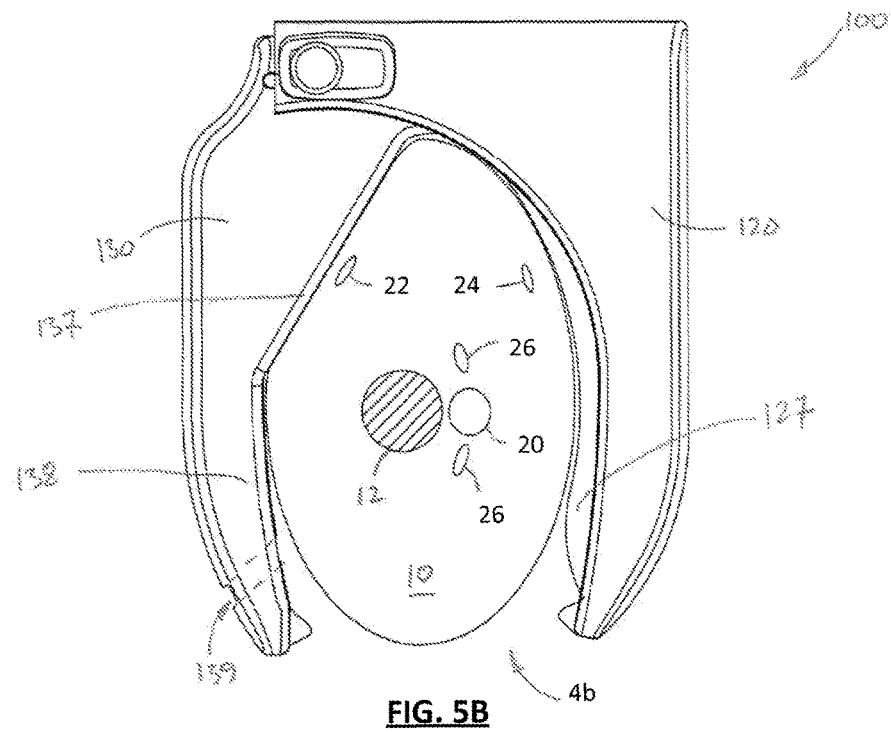
FIG. 5B is a schematic illustration of the clamping device similar to FIG. 5A but shown in a clamped position, in which the upper arm is compressed.
Figure 7:
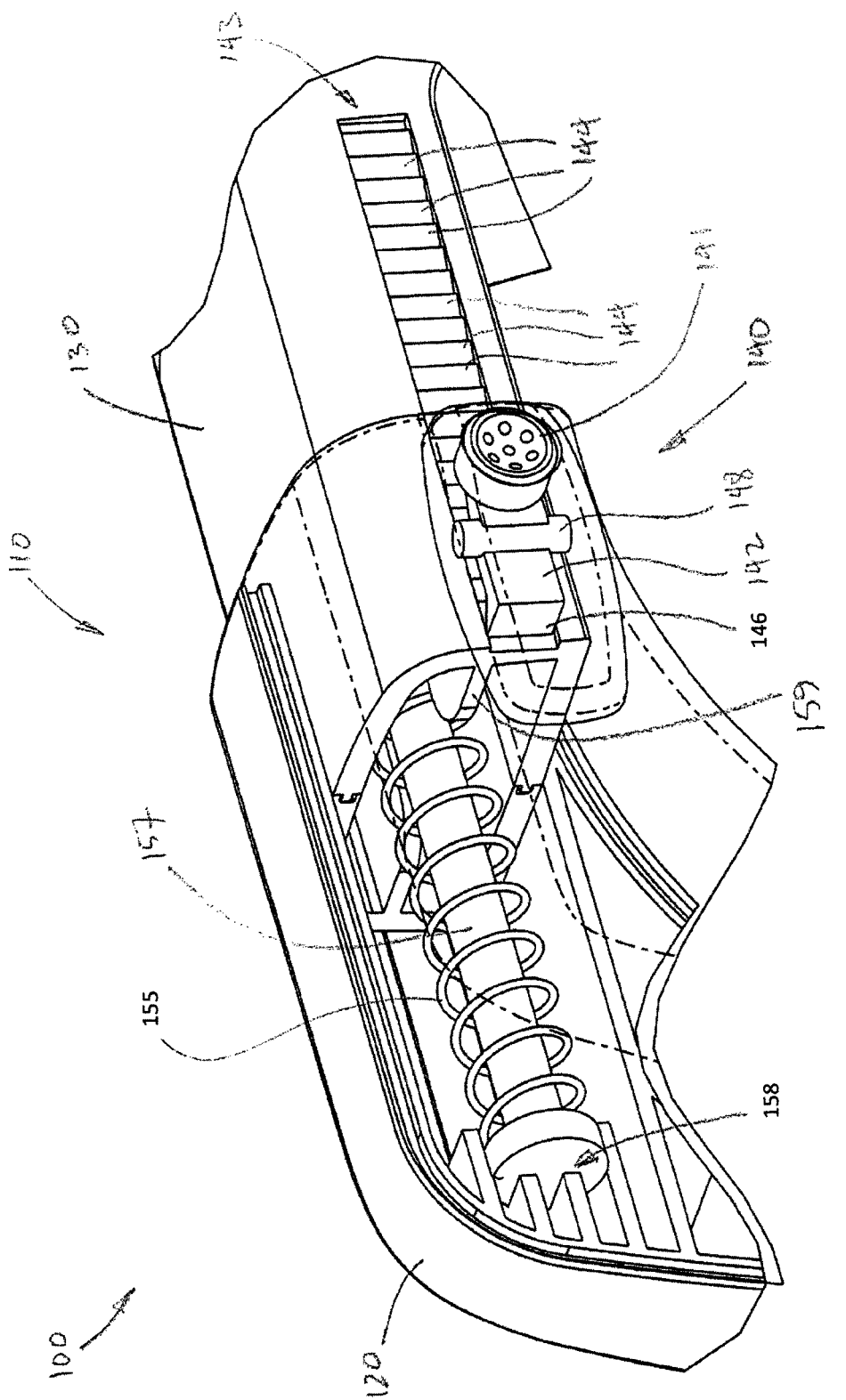
FIG. 7 is a partial cut away perspective view of the device of FIG. 2A illustrating biasing components and retention components.
Figure 8:
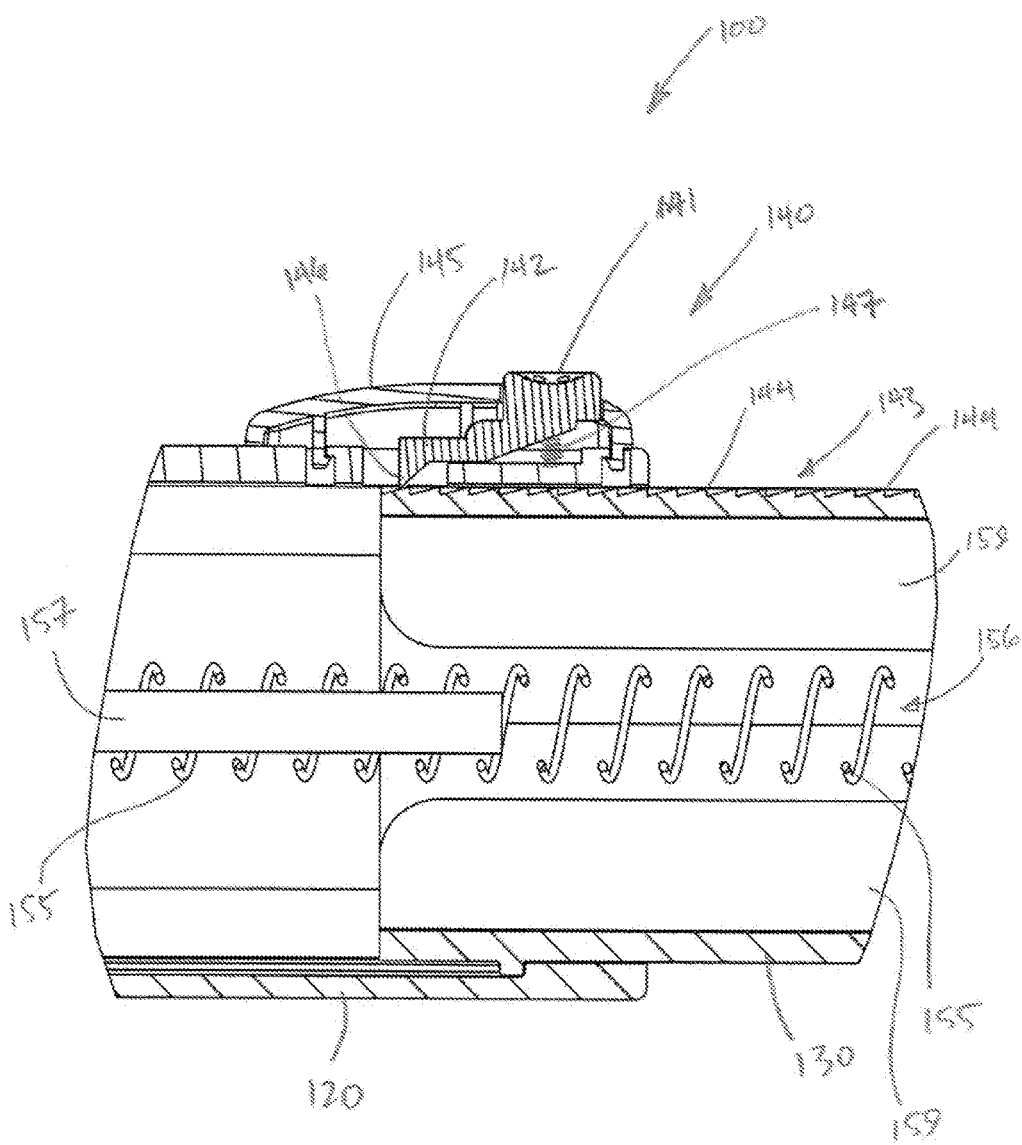
FIG. 8 is a cross-sectional view of part of the device of FIG. 2A further illustrating the biasing and retention components.

As shown in FIG. 2A and illustrated further in FIGS. 7 and 8, each retention mechanism 140 may comprise a ratcheting retention mechanism. This ratcheting retention mechanism 140 may comprise a linear rack 143 including a plurality of teeth 144 along which a pawl arm 142 travels between the clamped and unclamped positions. The pawl arm 142 comprises a manually releasable release actuator 141 at one end. The retention mechanism 140 comprises a biasing element 147 (FIG. 8) which cooperates with the pawl arm 142 to bias a pawl tooth 146 (on an opposite end of the pawl arm 142 from the release actuator 141) against the rack teeth 144. The pawl tooth 146 and rack teeth 144 are generally configured to permit relative movement of the pawl tooth 146 along the rack 143 in one direction, but tend to catch the pawl tooth 146 against one of the teeth 144 when a force might tend to cause relative movement in the opposite direction.

The pawl arm 142 further comprises a pawl pivot rocker 148 disposed intermediate the pawl tooth 146 and the release actuator 141 to allow the pawl arm 142 to pivot between an engaged position, in which the pawl tooth 146 catches against one of the teeth 144, and a release position, in which the pawl tooth 146 is free of interference from the teeth 144. The biasing element 147, which may be a spring for example, is positioned and configured to bias the pawl arm 142 toward the engaged position. A pawl cover 145 covers most of the pawl arm 142 from external interference, other than the release actuator 141, which is exposed for manual depression to move the pawl arm 142 to the release position. The pawl pivot rocker 148 may be received in a slightly recessed seat in (or otherwise held within the pawl cover 145 against) an external part of the first part 120.

The shape of the device 100 can be described as generally C-shaped or U-shaped, depending on the device orientation, featuring an opening between the opposed first and second distal portions 122, 132, with the bridge 110 at the apex opposite the opening. The space interior of the first and second jaws 120, 130 is thus generally concave to accommodate a limb and can be flattened as the jaws are pressed inwardly to close about the limb. At a minimum, at least one of the first inner profile 125 and the second inner profile 135 is generally non-linear. This non-linearity may take the form of a somewhat concave curvature along the respective jaw inner profile or a partially straight and partially curved profile. The first and/or second non-linear inner profile 125/135 may have two or more straight sections (angled relative to each other or separated by a curved section) and/or may have two or more sections of different curvature.

In the device embodiments 100 shown in FIGS. 2A to 5B, the first inner profile 125 is curved in a somewhat concave manner to be pressed against the medial surface of the arm and the second inner profile 135 has a first slightly curved section 136 near the bridge apex (corresponding to the coupling portion 110), a generally straight section 137 that is angled relative to the curved section 136 and angled relative to a longitudinal axis of the bridge (along which relative movement occurs) and a second slightly curved section 138 that is angled relative to the straight section 137 and extends to the distal end 132. The second curved section 138 may be generally straight in some embodiments. The straight section 137 need not be perfectly straight. The purpose of the straight section 137 is to apply direct pressure to the cephalic vein 22 when the device 100 is placed over an upper arm 10, as is most clearly illustrated in FIG. 5B. The configuration of the second inner profile 135, including straight section 137, is therefore arranged to apply pressure generally inwardly to the lateral side of the upper arm 10 but in particular to the top or upper lateral part of the upper arm 10.

Along with pressure applied to the lateral side of the arm by the second inner profile 135, the first inner profile 125 applies inward pressure to inwardly compress the medial side of the upper arm 10. In order to effectively compress the basilic vein 24 and the brachial veins 26, the first inner profile preferably has a ridge, projection or bead 127 extending along the inner surface of the first jaw 120 between its distal end 122 and a point close to, but still somewhat distal of, the bridge portion 110. This ridge, projection or bead 127 serves to focus the pressure applied to the medial side of the arm and thereby more effectively compress the veins on the medial side of the upper arm 10.

Device 100 may have a cushioning element 160 that extends around (or mostly around) an inner periphery of the bridge 110 and first and second arms 120, 130. This cushioning element 160 may cover the ridge, projection or bead 127 on the first jaw 120 and may be affixed to the first jaw 120 at one more points. The cushioning element 160 may be freely slidable with respect to the second jaw 130 along the second inner profile 135 to allow for accommodating the relative movement between the first and second jaws during clamping and unclamping.

The second jaw 130 may have formed in its distal end 132 a passage 139 to receive an end portion 162 of the cushioning element 160. The passage allows travel of the cushioning element 160 through the distal end passage 139 as the cushioning element 160 moves along the second inner profile 135 during clamping or unclamping. This way, the end portion 162 does not interfere with the patient's arm during the clamping action and the cushioning element 160 experiences minimal or no bunching and there is minimal or no pinching of the arm by the cushioning element 160.

FIG. 2B illustrates an example cross-section of the cushioning element 160 along the length of it where it overlies the second inner profile 130. The cushioning element may have a backing layer 161 and a cushioning layer 164. Along at least part of the cushioning element 160, the backing layer 161 may have a length-wise bead 163 projecting inwardly (away from a flat backing section of the backing layer 161) toward the space 115. This bead 163 may provide a similar function to the ridge 127 in focussing compression on the arm.

Referring in particular to FIGS. 7 and 8, the internal structure of the coupling portion 110 is described in further detail. In order to bias the device 100 into the open position, a biasing element, for example in the form of a spring 155, is positioned to bias the first and second parts 120, 130 away from each other. In particular, the biasing element biases first and second portions of the coupling portion 110 away from each other. Since these first and second portions of the coupling portion 110 are attached to or integrally formed with the first and second parts 120, 130, the first and second parts 120, 130 are biased away from each other under the action of the biasing element.

The internal structure of the first and second parts 120, 130 is arranged to accommodate the biasing means extending longitudinally inside both the first part 120 and the second part 130 in a manner that may be generally parallel to a back or spine of the body 101 of the device 100. In order to retain the biasing element (in the form of spring 155) in position, a rod seat 158 is provided internally at one end of the device body 101 to receive one end of a bias element alignment rod 157. The other end of the bias element alignment rod 157 extends at least part-way into a cavity or chamber defined by the second part 130. The spring 155 is coiled around at least part of the bias element alignment rod 157 so that compression and extension of the spring 155 within the first part 120 generally occurs along the rod 157, as shown in FIGS. 7 and 8. The bias element alignment rod 157 may be sized to act as a stop to prevent relative movement of the first and second parts past a certain point, for example by abutting an internal structure of the second part.

The second part 130 defines an internal cavity or chamber with wall and/or flange structures 159 defining a spring channel 156 through which the spring 155 extends. Such wall/flange structures 159 serve an alignment function to keep the spring 155 generally longitudinally aligned during compression and extension within the second part 130.

Figure 6:
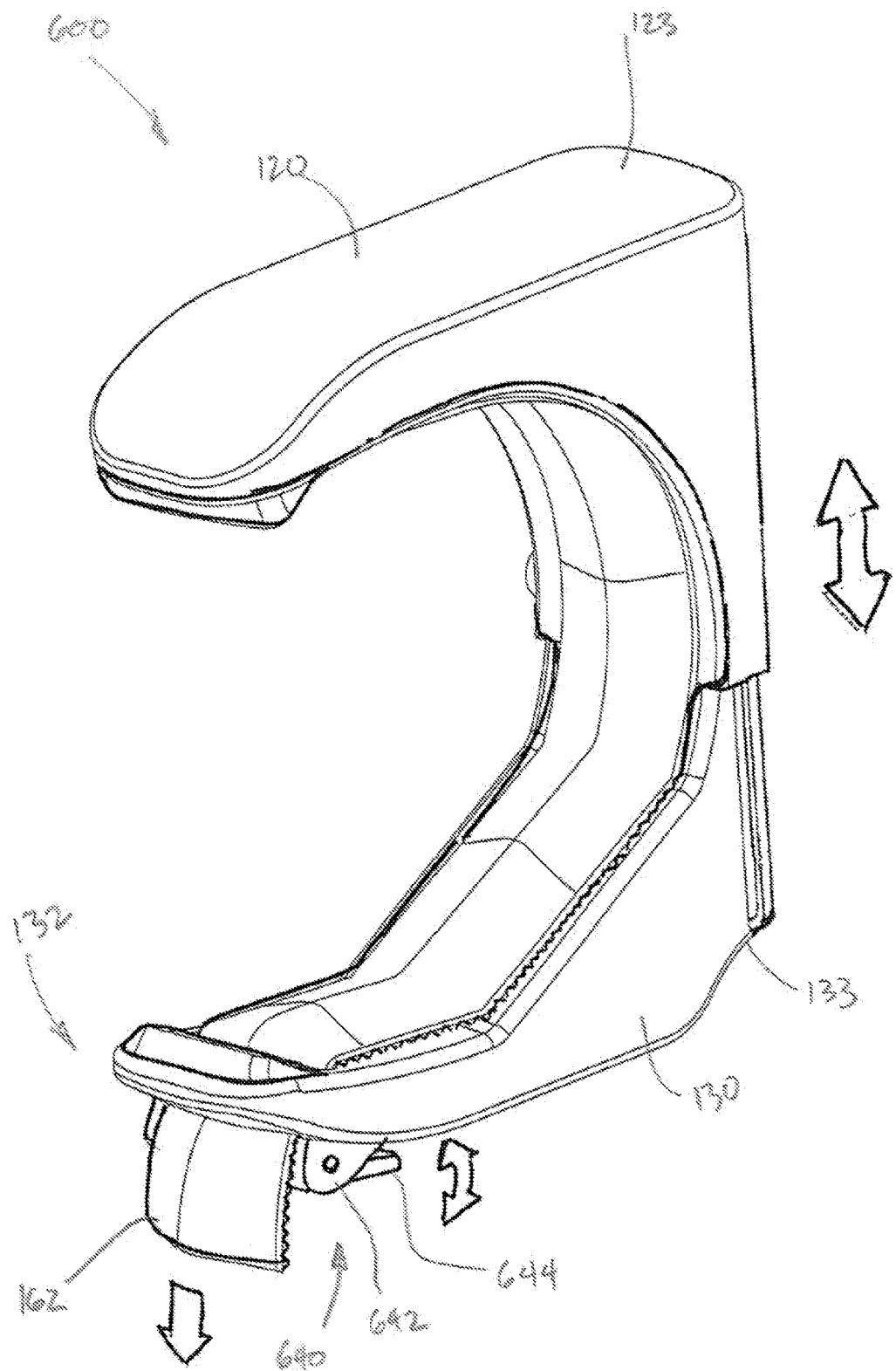
FIG. 6 is a perspective view of a clamping device according to some alternative embodiments.

Referring now to FIG. 6, an alternative or additional retention mechanism 640 is shown, by which a clamping device 600 can be retained in a clamped position. The clamping device 600 may be identical to the clamping device 100, except that it uses the modified retention mechanism 640 as an alternative or addition to the retention mechanism 140 described in relation to device 100.

The retention mechanism 640 comprises a frictional retention mechanism that acts to frictionally engage the liner tongue 162 on an external side of the liner tongue passage 139. The retention mechanism 640 may comprise a spring biased lever 644 that pivots about a pivot axis that is generally parallel to the lateral extent of the liner tongue 162 and the external surface of the distal end 132 of device 600.

At least one anchor component 642 is formed or mounted on the external surface of the distal end 132 adjacent the external outlet side of the passage 139, so that when the anchor component 642 secures the lever 644 to rotate about the lateral pivot axis, a cam (formed on a part of the lever 644 adjacent where the liner tongue 162 projects) is arranged to impinge on and frictionally engage with the back side of the liner tongue 162 when the lever 644 is biased into a retaining position. The cam of the lever 644 is arranged so that the liner 160 can be pulled further through the passage 139 without significantly increasing the frictional engagement between the cam and the back of the liner 160, which serves to retain the device 600 in the clamped position.

Forces that would tend to push the device toward the unclamped position are resisted by increased frictional engagement of the cam (under the rotational spring biasing force of the lever 644) with the back of the liner 160 when the liner 160 is effectively pulled relative to the second part 130 toward an internal side of the second part 130. In order to release the retention mechanism 640, the lever 644 may be depressed, which moves the cam on the other end of the lever 644 away from a frictionally engaging position with the liner 160, thereby allowing the liner 160 to be easily withdrawn back through the passage 139 as the device opens from the clamped position to the unclamped position.

Figure 9:
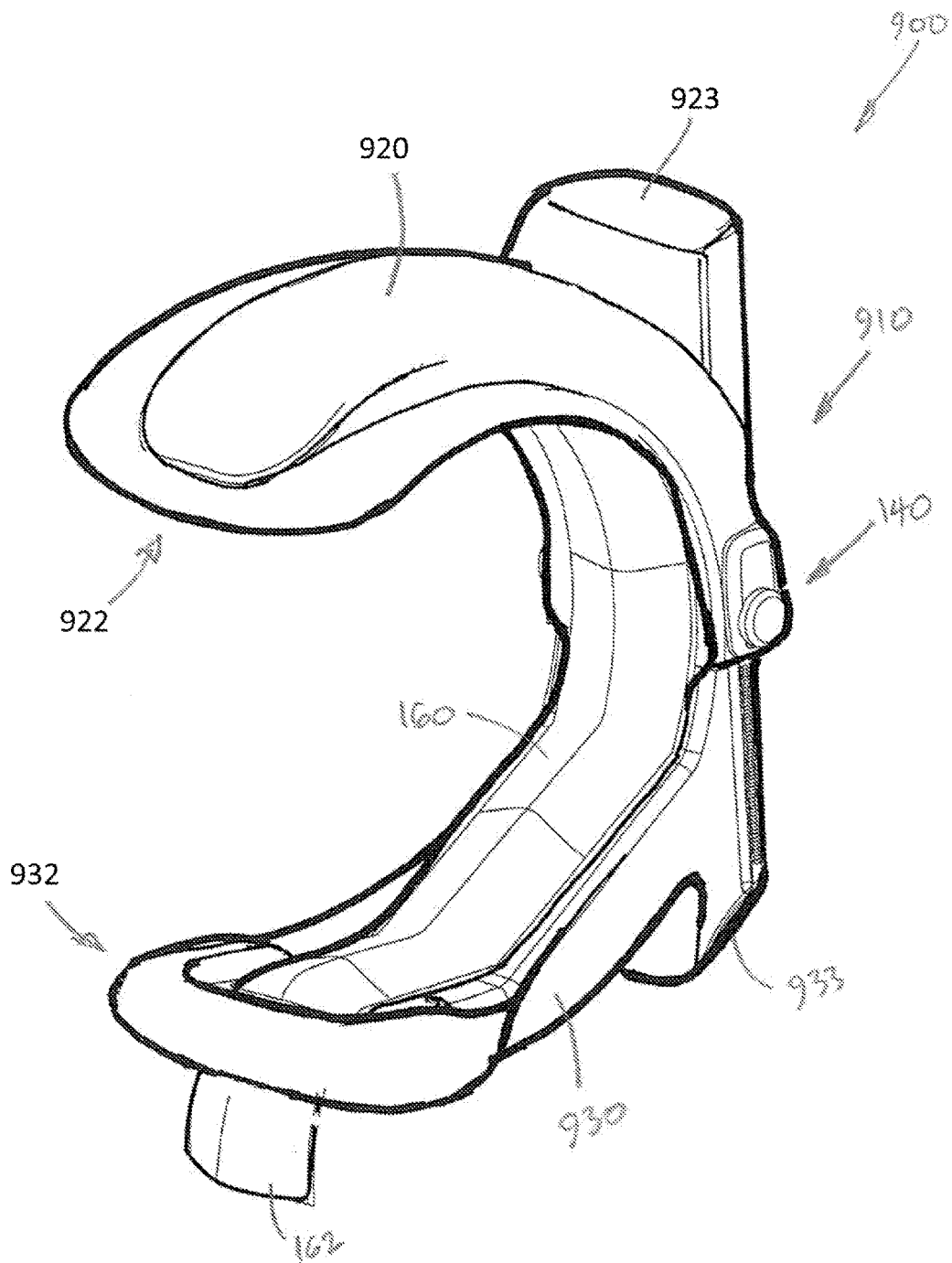
FIG. 9 is a perspective view of a clamping device according to further alternative embodiments.

Referring now to FIG. 9, further clamping device embodiments are shown and described, in the form of an example clamping device 900. The clamping device 900 is quite similar to devices 100 and 600, but has accentuated curvature and padding around distal first and second ends 922, 932 of respective first and second parts 920, 930. A coupling or bridge portion 910 joins the first and second parts 920, 930 in a similar manner to devices 100 and 600, as described above. Additionally, device 900 is shaped to have easily recognisable and graspable lands 923 and 933 on opposite ends of the device 900 to readily allow manual compression of the device from an unclamped position (or a partially clamped position) to a fully (or more fully) clamped position by squeezing together of a person's thumb and fingers. It can thus be observed from FIG. 9 that the described embodiments of the clamping device need not be exactly in the form shown in FIGS. 1 to 8, but may accommodate some variation in shape and configuration while performing a similar function.

Figure 10:
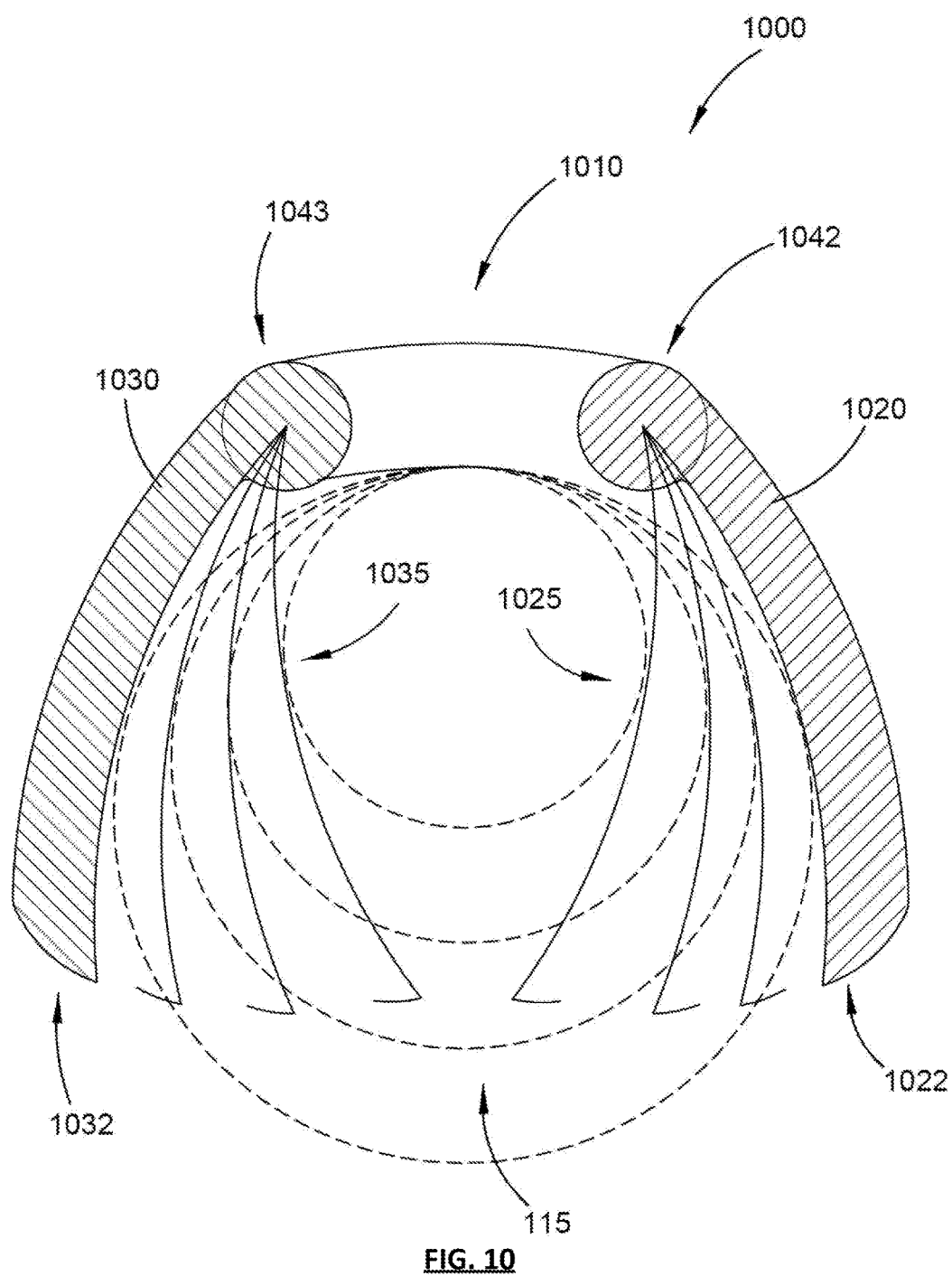
FIG. 10 is a schematic illustration of a clamping device according to still further embodiments.

Referring now to FIG. 10, a clamping device 1000 according to further embodiments is shown and described. The clamping device 1000 is shown schematically for illustration purposes to have a bridge portion 1010 to which are rotatably coupled first and second movable jaws 1020 and 1030. The jaws 1020, 1030 are independently movable relative to each other and to the bridge portion 1010 so that they can adopt an open position in order for the device 1000 to be placed about a portion of a limb, such as an upper arm, and a closed or clamped position, where the device 1000 has the first and second jaws 1020, 1030 pressing against the limb, such as on medial and lateral sides of the limb.

In a generally analogous form to the clamping devices 100, 600 and 900 shown and described herein, the clamping device 1000 employs a form of retention mechanism to retain the device 1000 in the clamped position. In the illustrated embodiments of clamping device 1000, first and second retention mechanisms 1042 and 1043 are employed, for example, in the form of respective ratcheting retention mechanisms that allow progressive rotation of each of the first and second jaws 1020, 1030 in the clamped position but resist movement back into the unclamped position unless a manually actuable release mechanism, such as a depressible button (not shown) is actuated.

Similarly to the clamping device embodiments described above, the first and second jaws 1020, 1030 of clamping device 1000 may have a non-linear inner profile where those jaws are arranged to impinge on the surface of the limb to be clamped. This non-linear profile may be provided on one or both of the inner faces of the first and second jaws 1020, 1030. The non-linear profiles of the rigid jaws 1020, 1030 may take the form of a generally concave surface (optionally with a projecting ridge analogous to ridges 127 and 163). Alternatively, one or both of the inner profiles of the rigid jaws 1020, 1030 may have a series of straight portions angled with respect to each other to in effect define a roughly concave inner profile. Alternatively, the inner profile may have at least one curved section and at least one straight portion.

Figure 11A:
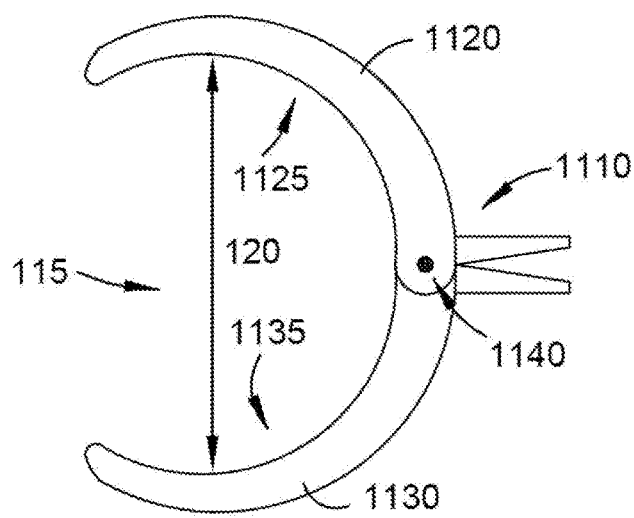
FIGS. 11A, 11B and 11C are schematic illustrations of a clamping device according to still further embodiments, showing open, partially clamped and fully clamped positions.
Figure 11B:
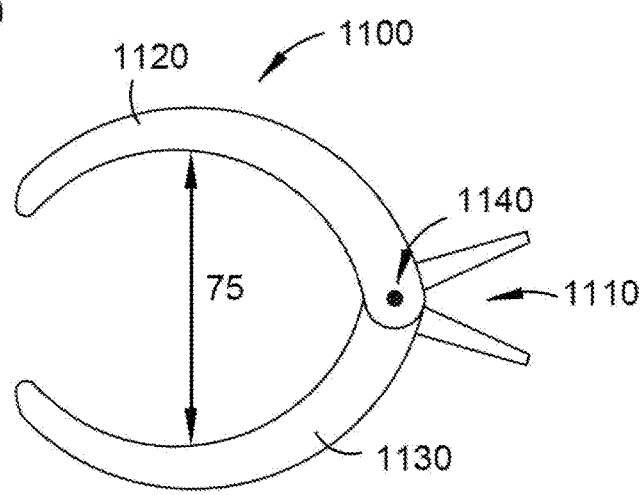
Figure 11C:
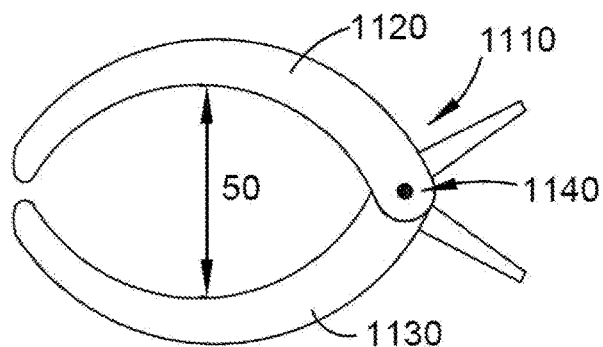

Referring now to FIGS. 11A, 11B and 11C, a clamping device 1100 according to further embodiments is described. Clamping device 1100 has a bridge or coupling portion 1110 that defines a pivot axis about which first and second opposed jaws 1120, 1130 may rotate relative to each other when moving between a clamped position and an unclamped position. As with other embodiments described herein, the opposed first and second jaws 1120, 1130 define a space 115 therebetween in the unclamped or open position in order to allow the device 1100 to be placed about a limb. The first and second inner profiles 1125, 1135 of the respective first and second jaws 1120, 1130 are shown as being generally curved in a concave form, although the concave form may be achieved by including one or more straight portions and/or more than one curved section in order to provide more targeted compression of particular veins in the limb to be clamped.

The clamping device 1100 may employ a retention mechanism 1140 that includes a rotationally ratcheting retention mechanism. Although not shown, a manually actuable release mechanism, such as a depressible button, may be used to allow the device 1100 to adopt the unclamped position (from the clamped position) under the action of a suitable biasing element, such as a spring (not shown).

Figure 12:
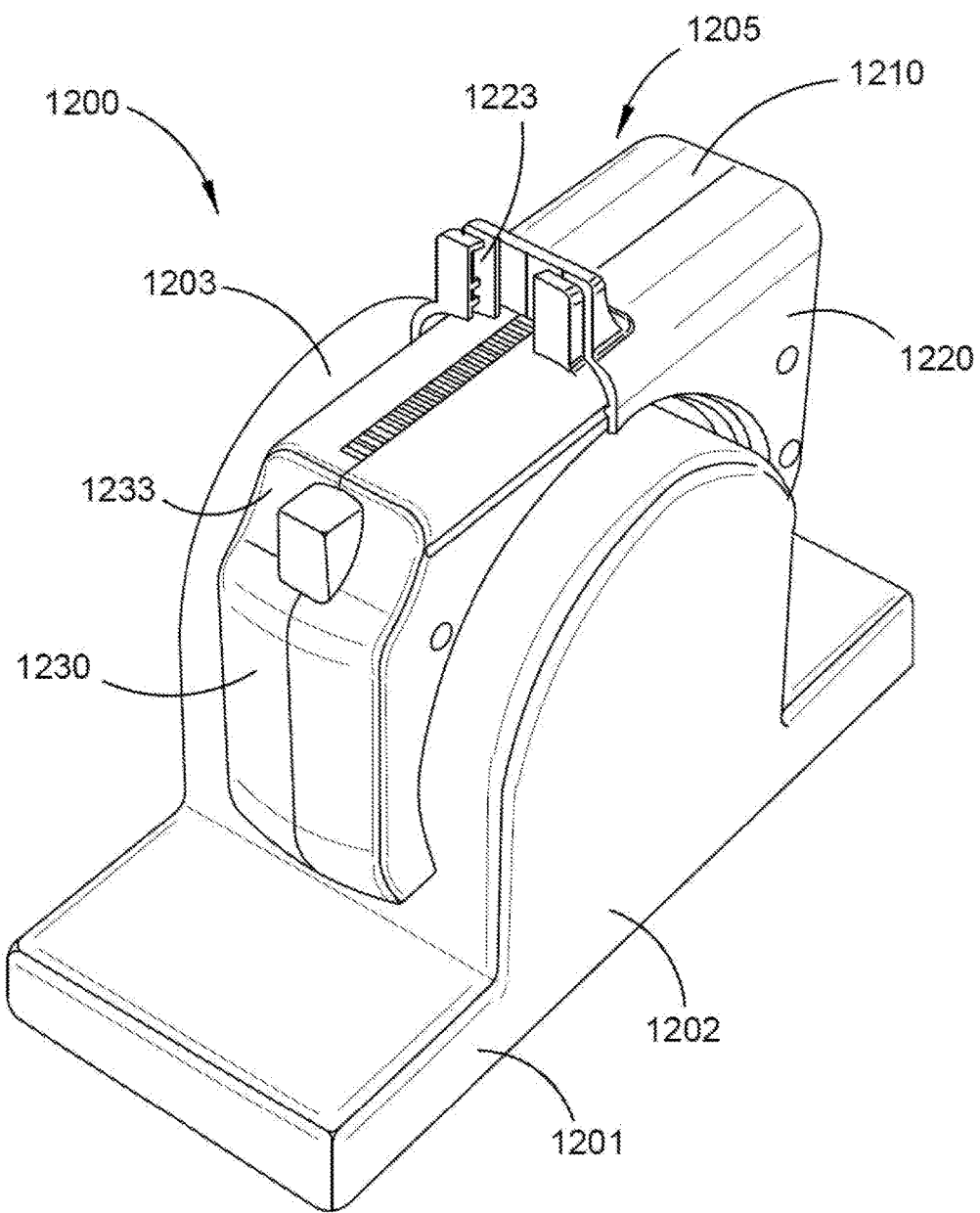
FIG. 12 is a schematic illustration of a kit comprising a cradle and a clamping device according to some embodiments mounted or positioned on the cradle.

According to some embodiments, the clamping device may be accompanied by kit components that may assist in hygienic storage and use of such clamping devices. As shown in FIG. 12, for example, a saddle device 1201 may be provided as part of a kit 1200 that also includes a clamping device 1205 according to still further embodiments. The saddle 1201 may comprise a generally horizontal base portion 1202 for placement on a flat surface and a generally upwardly projecting convex portion 1203 of a size and shape to generally match and fit within the space 115 defined between first and second jaws 1220, 1230 of the device 1205 when it is in the open unclamped position.

The clamping device 1205 shown in FIG. 12 may define oppositely directed lands 1223 and 1233 on respective first and second parts 1220, 1230 that are not at opposite ends of the device body but are instead positioned more closely together along a spine region 1210 (analogous to the bridge coupling portion of the clamping device embodiments described above). Thus, the lands used to manually compress the device into the clamped position need not necessarily be located at opposite ends of the clamping device but may instead be defined by one or more projecting portions that are of suitable orientation for manual engagement of a thumb and fingers in a squeezing action.

Referring now to FIGS. 13A, 13B and 14, a clamping device 1300 according to further embodiments is shown and described, as part of a kit comprising a disposable clamp liner 1360. The kit may comprise multiple such disposable liners 1360 contained in a suitable container 1400, for example.

The clamping device 1300 functions in a generally similar manner to the clamping device embodiments described above in that it has a bridge or coupling portion 1310 that joins opposed first and second jaws 1320, 1330 in a manner that allows them to move between a clamped position and an unclamped position. A retention mechanism 1340 (in this case a linear ratcheting mechanism with a release actuator similar to that described and shown in relation to FIGS. 1 to 5, 7 and 8) is used to retain the device 1300 in the clamped position.

Clamping device 1300 may have an elastomeric overmould 1323 formed or fitted onto or around most of the device body, including the first and second generally rigid jaws 1320, 1330. This over-mould 1323 may comprise a material with a relatively high co-efficient of friction with respect to human skin so as to improve gripability (frictional characteristics) of the device 1300 when applying the device 1300 to clamp a limb. Suitable compression ridges may be formed to project from one or both of the inner profiles of the first and second jaws 1320, 1330.

A recess or detent 1339 may be formed in an external surface toward a distal end of one of the first and second jaws 1320, 1330. This recess or detent 1339 is shown in FIG. 13A and in FIG. 13B by way of example as being in an external surface of the first jaw 1320. This recess or detent 1339 is sized and arranged to receive a folded end portion 1362 of one of the flexible disposable liners 1360, so that the remainder of the liner 1360 can be pressed or folded into the space 115 and generally overly the U-shaped inner profile defined by the opposed first and second jaws 1320, 1330 in the clamped and unclamped positions. The end of the disposable liner 1360 that is not received in the recess or detent 1339 is left as a free end so that movement of the liner 1360 at its free end is allowed in order to mitigate pinching of the limb as the device 1300 moves towards the clamped position.

In order to at least partially temporarily affix the disposable liner 1360 to the device 1300, an adhesive substance may be provided on a back surface (opposite to a limb engaging surface of the liner 1360) to adhere the liner 1360 to the same jaw (eg, the first jaw 1320) which retains the one end 1362 of the disposable liner 1360. This adhesive substance may be exposed by removal of a peel away backing sheet, for example, and should not be so strong as to make manual removal of the liner 1360 from the device 1300 difficult.

The container 1400 of disposable liners 1360 may include a number of such liners 1360 in a ready to remove form, so that each liner can be removed from a body 1410 of the container 1400 through a top and/or side aperture 1415. The disposable liners 1360 may be arranged in the container 1400 in a manner that allows the one end 1362 (to be received in the recess or detent 1339) to be readily identified and used as a means to withdraw the disposable liner 1360 from the container 1400.

Figure 15:
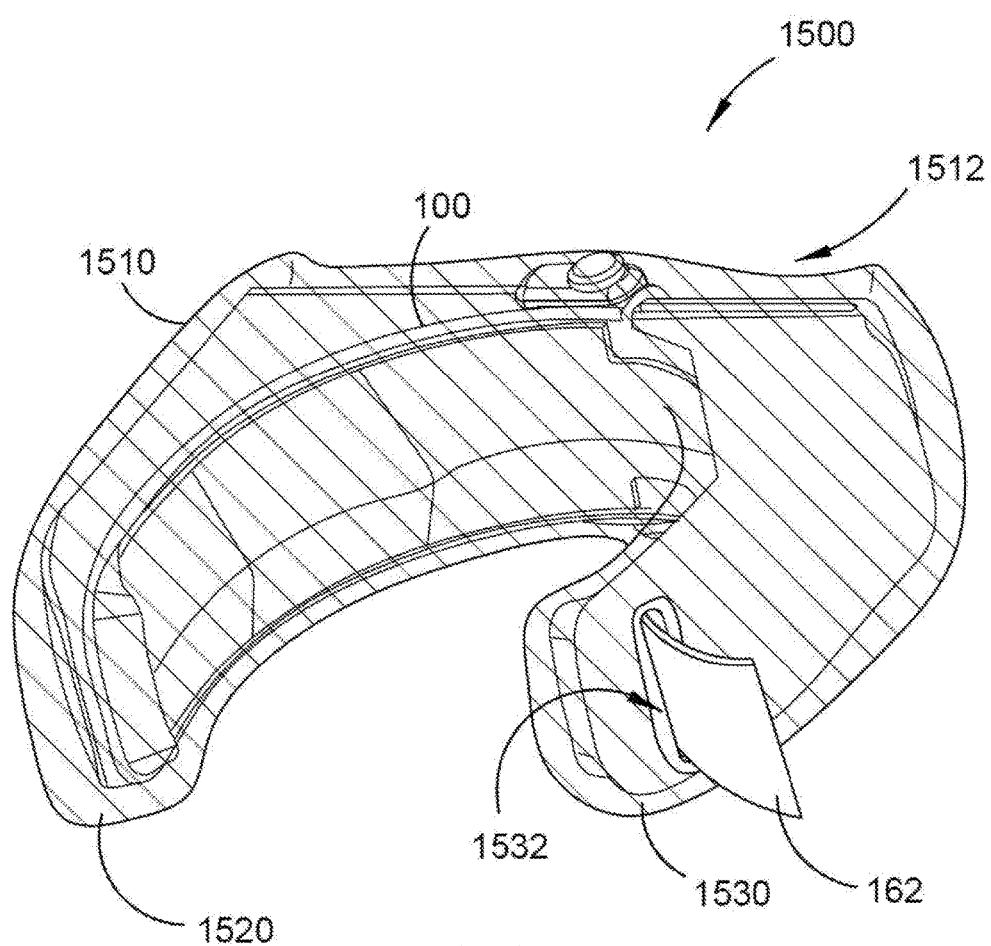
FIG. 15 is a schematic illustration of a kit comprising a disposable clamp cover according to some embodiments and the clamping device of FIG. 2A.

Referring now to FIG. 15, a further form of disposable liner 1510 is shown and described as part of a kit 1500 that also includes the clamping device 100 (as one example of various described clamping devices usable with the disposable liner 1510). The disposable liner 1510 may be roughly in the form of a flexible plastic sack that substantially covers most of the body of the device 100, but for an opening 1512 along the backside or spine of the device 100. The opening 1512 exposes an opposite face of the device 1300 to the inner apex of the U-shape defined by the first and second parts 120, 130.

The disposable liner 1510 defines opposed pouch portions 1520 and 1530 for receiving and substantially enclosing the opposed first and second portions 120, 130, respectively, with a bridging section that joins the two pouch portions 1520, 1530. In this way, the entire inner U-shaped clamping profile of the device 100 is covered by the disposable liner 1510, while the liner 1510 remains easily pulled off the device 100 by withdrawing the device 100 from the sack through the opening 1512 in the back of the liner 1510. Optionally, the second pouch portion 1530 may have a slit or aperture 1532 formed in an outer side thereof to allow the liner tongue 162 to extend therethrough.

The disposable liner 1510 is preferably formed of a hygienic plastic or fabric material that is easy to put on and taken off and does not impede or interfere with the clamping and unclamping actions of the clamping device 100 (or other embodiments described and depicted herein).

Kit 1500 may comprise multiple disposable liners 1510 arranged in a stack so as to be sequentially opened out and pulled off the stack as each successive disposable liner 1510 is used. Although not shown, preferably the kit 1500 includes a holding device, similar to those currently known and in use for plastic shopping bags and umbrella sleeves, to hold the stack of disposable liners 1510 so that, as the clamping device 100 (or any other clamping device embodiments described herein) is inserted with its jaws into the pouches 1520, 1530 of the disposable liner 1510 and pulled away from the rest of the stack of such liners, another liner is pulled into a position ready for similar use.

Referring now to FIGS. 16A, 16B, 17A, 17B, 18, 19 and 20, a clamping device 1600 according to some further embodiments is shown and described. The clamping device 1600 operates on similar principles to the clamping devices described above and includes a coupling or bridge portion 1610 that couples a first jaw 1620 with a second jaw 1630 in a manner that allows relative movement of the first and second jaws 1620, 1630 between clamped and unclamped positions.

The clamping device 1600 has a retention mechanism 1640 to retain the device 1600 in the clamped position. This retention mechanism 1640 may be a ratcheting retention mechanism, for example. The ratcheting retention mechanism may comprise a loop 1643 that has ratchet teeth 1644 linearly disposed to progressively engage with at least one lateral pawl projection 1646 on one of the first and second jaws 1620, 1630. The loop 1643 is anchored at an anchor point 1645 adjacent a shoulder of the other one of the first and second jaws 1620, 1630 in the example illustrated. The loop 1643 is anchored at the anchor point 1645 adjacent a shoulder of the first jaw 1620 in a manner that allows pivoting of the loop 1643 about the anchor point 1645. This allows the loop 1643 to move with the second jaw 1630 as it rotates about a rotatable coupling 1641 that connects the first and second jaws 1620, 1630 and forms part of coupling portion 1610.

Figure 18:
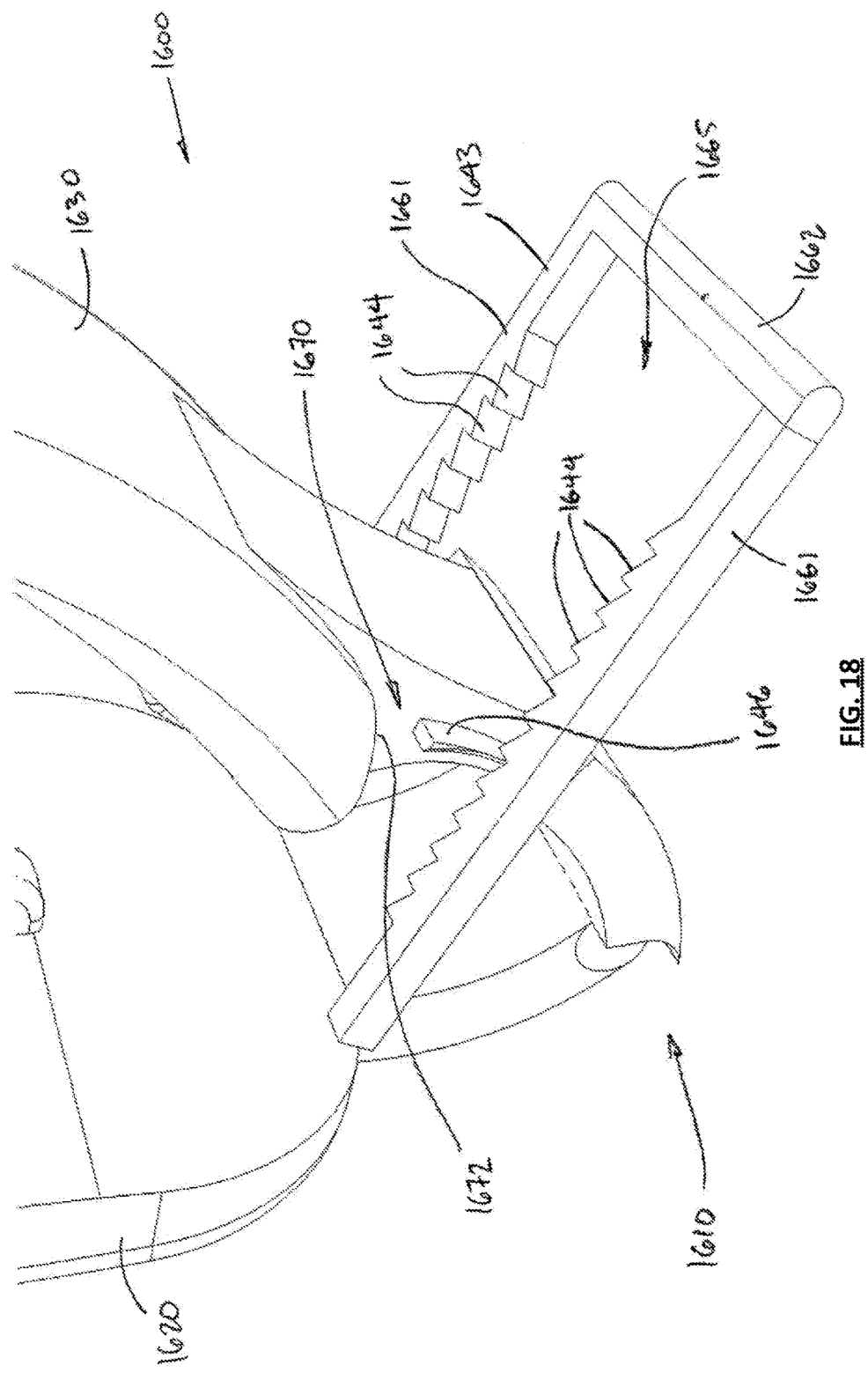
FIG. 18 is a close up perspective view of a retention mechanism of the clamping device of FIG. 16A.
Figure 19:
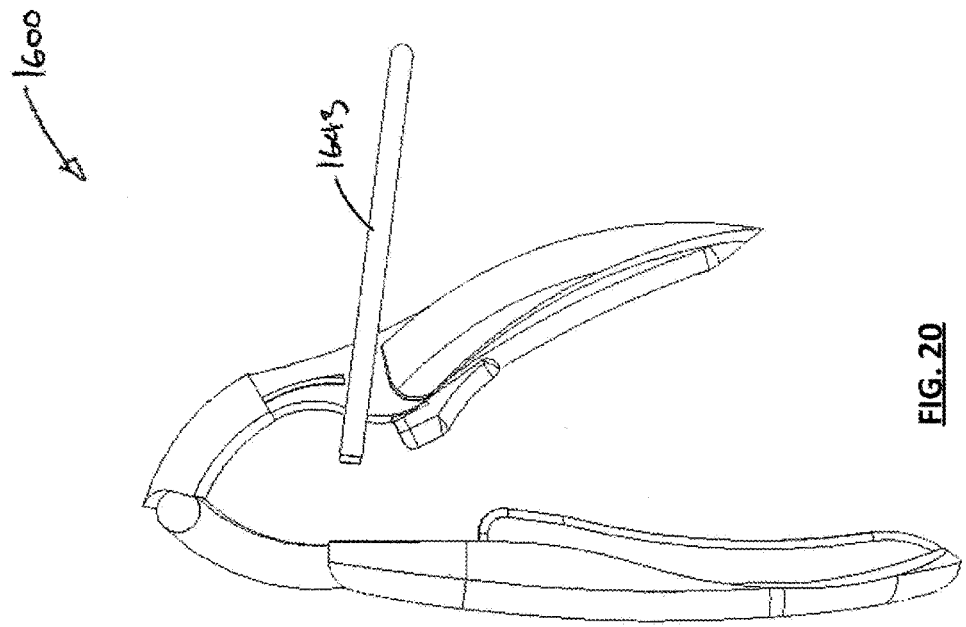
FIG. 19 is a side view of the clamping device of FIG. 16A, shown in a clamped position and illustrating a release position of the retention mechanism to allow the device to adopt the unclamped position.
Figure 20:
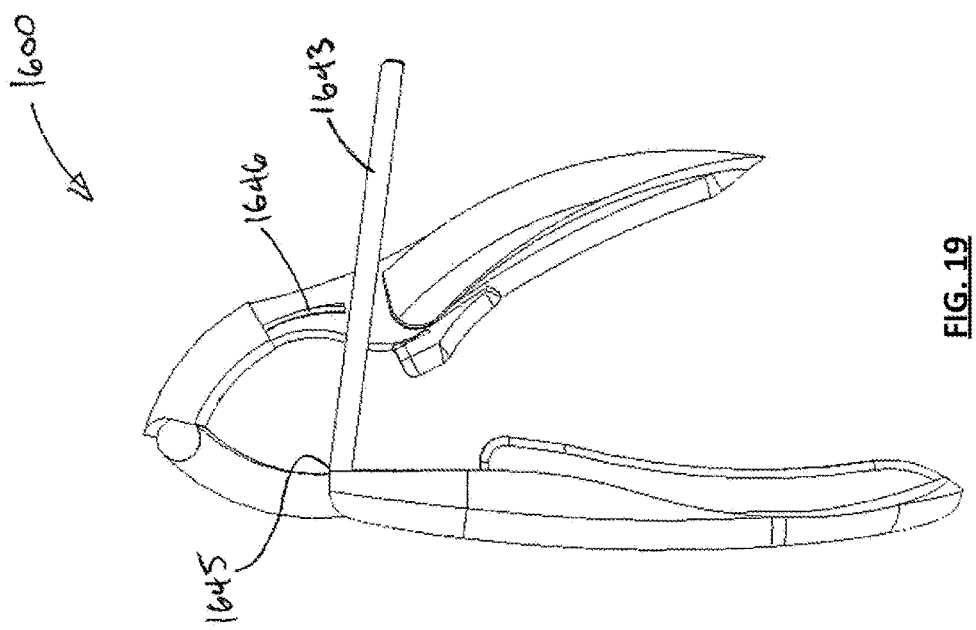
FIG. 20 is a side view of the clamping device of FIG. 16A, shown in a clamped position and illustrating a breakaway release of the retention mechanism to allow the device to adopt the unclamped position.

The shape of the pawl projection 1646 is most visible in FIG. 18. In order to allow the clamping device 1600 to return to the unclamped position from the clamped position, the loop 1643 can be pivoted to a release position beyond one edge of the pall projections 1646 so that the teeth 1644 no longer engage with the pawl projections 1646. In this release position, the loop 1643 aligns with a gap 1670 formed in between one end of the pawl projections 1646 and an adjacent shoulder 1672 of the second jaw 1630. This is illustrated in FIG. 19. Alternatively or additionally, the loop 1643 may be connected to the first jaw 1620 in a manner that allows the loop 1643 to be broken away or detached from the first jaw 1620 at the anchor point 1645 or another part of the loop 1643, as illustrated in FIG. 20. In such embodiments, where the device 1600 is intended to only allow a single use, the gap 1670 may not be present and the frangible attachment of part or all of the loop 1643 to the first jaw 1620 may assist in ensuring that the device 1600 is not used multiple times, since the broken loop 1643 would not operate to retain the device 1600 in the clamped position.

As shown best in FIG. 18, the loop 1643 comprises opposed linear sets of ratcheting teeth 1644 arranged on generally parallel linear ratchet arms 1661, which are joined at an outer apex of the loop 1643 by an end loop or bar 1662.

As is evident from the drawings, some clamping device embodiments shown and described herein are asymmetrical about the apex of the U-shape of the device, such that one jaw may be differently shaped and sized from the other jaw. This may in some embodiments assist targeted compression of certain veins in the limb to be compressed.

As shown in FIGS. 16A to 20, clamping device 1600 is generally asymmetrical, with the first jaw 1620 being longer than the second jaw 1630 and configured to press against a medial side of an upper arm, as illustrated in FIG. 16B. On the other hand, the second jaw 1630 is arranged to be pressed against an upper lateral part of the upper arm in order to target compression of the cephalic vein 22 while the first jaw 1620 targets compression of the basilic and brachial veins 24 and 26.

Thus, the clamping device 1600 is sized and arranged such that, when the limb is an upper arm and the device 1600 is placed in the clamped position about the upper arm with one of the first and second jaws 1620, 1630 pressing against a medial side of the upper arm, the other of the first and second jaws 1620, 1630 presses against an upper lateral part of the upper arm to compress the cephalic vein.

As shown in FIGS. 16A to 20, device 1600 has a first longitudinal ridge 1627 projecting from an inner profile of the first jaw 1620 in order to target compression of the veins on the medial side of the limb, while the second jaw 1630 has a ridge 1663 positioned to target compression of the cephalic vein 22 on a top lateral side of the upper arm.

As illustrated in the Figures, most of the clamping device embodiments are not intended to have the distal ends of the jaws touch each other when in the clamped position. Thus, at least some of the described clamping device embodiments are generally not arranged to entirely encircle the limb, nor are they arranged to contact and compress the entire circumference or periphery of the limb.

As shown in FIGS. 16A to 20, the clamping device 1600 has generally slightly concavely curved inner profiles where the first and second jaws 1620, 1630 are to contact the limb. In alternative embodiments, such first and second inner profiles may have portions of different curvature and/or generally straight sections.

Figure 21:
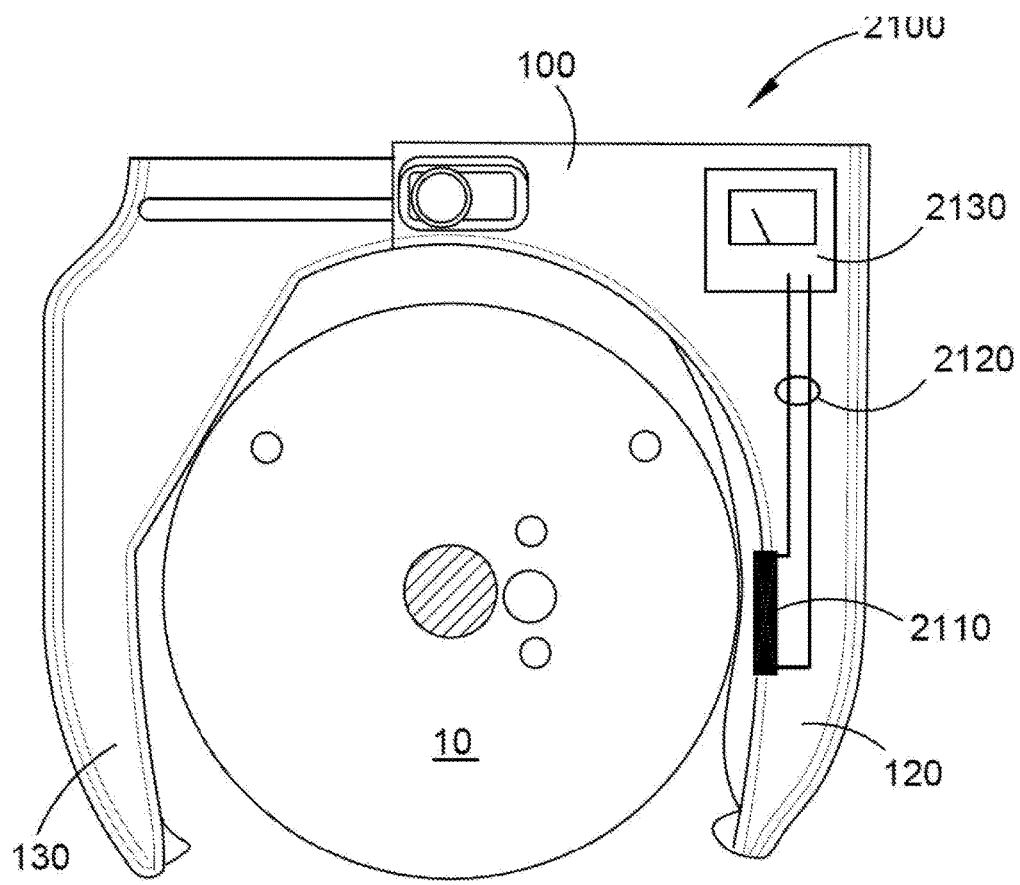
FIG. 21 is a schematic view similar to FIG. 5A but illustrating a further example clamping device that includes a pressure sensor.
Figure 22:
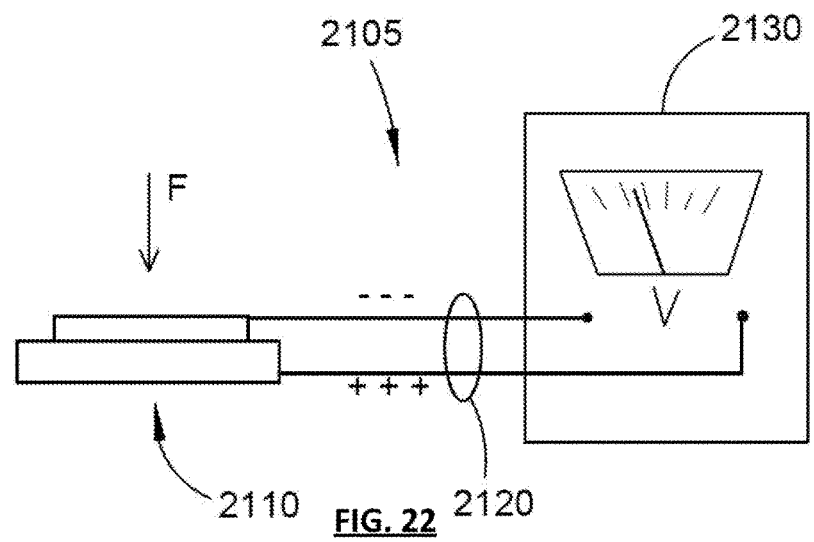
FIG. 22 is an example schematic circuit diagram of the pressure sensor shown in FIG. 21.

Referring now to FIGS. 21 and 22, an example clamping device 2100 is shown, including a pressure sensor 2105 arranged to sense pressure on a part of the inner profile or inner face of one or both of the first and second jaws 120, 130. The clamping device 2100 may be the same as device 100, but for the inclusion of the pressure sensor 2105. Alternatively, the pressure sensor 2105 may be incorporated within other clamping device embodiments described herein and suitably arranged to sense a clamping pressure applied to a limb when the clamping device is in a clamped position on the limb.

The pressure sensor 2015 comprises a pressure transducer element 2110, which can be a piezoelectric element, for example. The pressure transducer element 2110 may be electrically coupled via suitable insulated conductors 2120 to provide an output signal indicative of the sensed pressure to a display 2130. The display 2130 is arranged to indicate (in response to the received output signal) the pressure sensed by the transducer element 2110, so that a person, such as a medical practitioner, can readily view the display 2130 and ascertain whether the clamping device 2100 has been applied with too much compression, not enough compression or a degree of compression that is appropriate.

Although the pressure sensor 2105 is shown in FIG. 21 as being disposed in the first part or jaw 120, with the pressure transducer element 2110 being positioned adjacent the inner face or ridge extending along the inside of the first part or jaw 120, the pressure transducer element 2110 may be positioned at a different position around the inner profile of the clamping device 2100. Additionally, more than one pressure transducer element 2110 may be positioned around the inner profile of the clamping device 2100, either coupled via additional conductors 2120 to the same display 2130 or as part of multiple separate pressure sensors 2105.

Figure 23A:
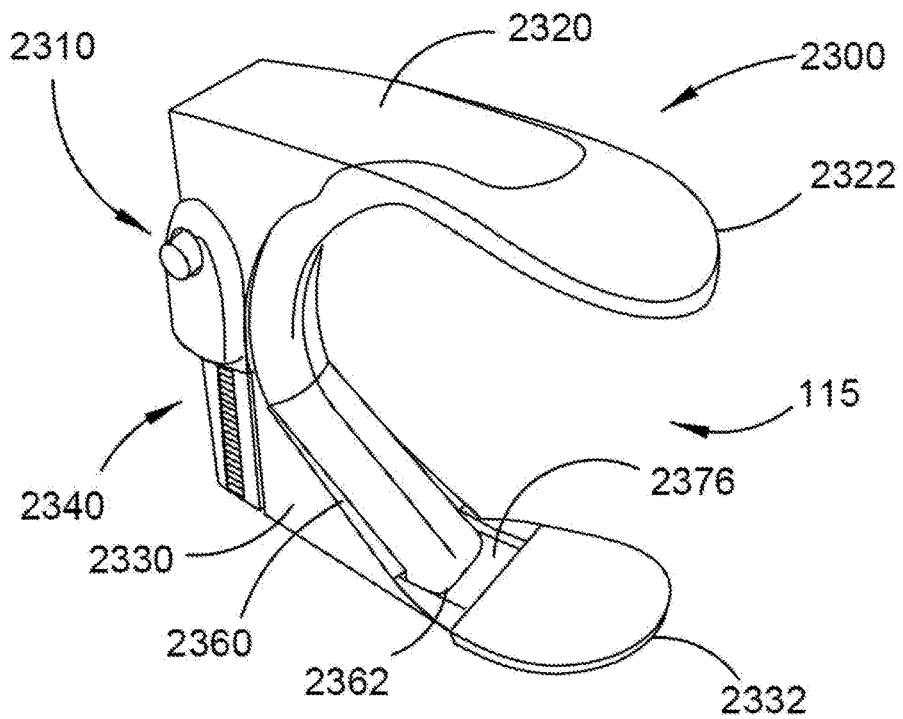
FIG. 23A is a perspective view of a further example clamping device.
Figure 23B:
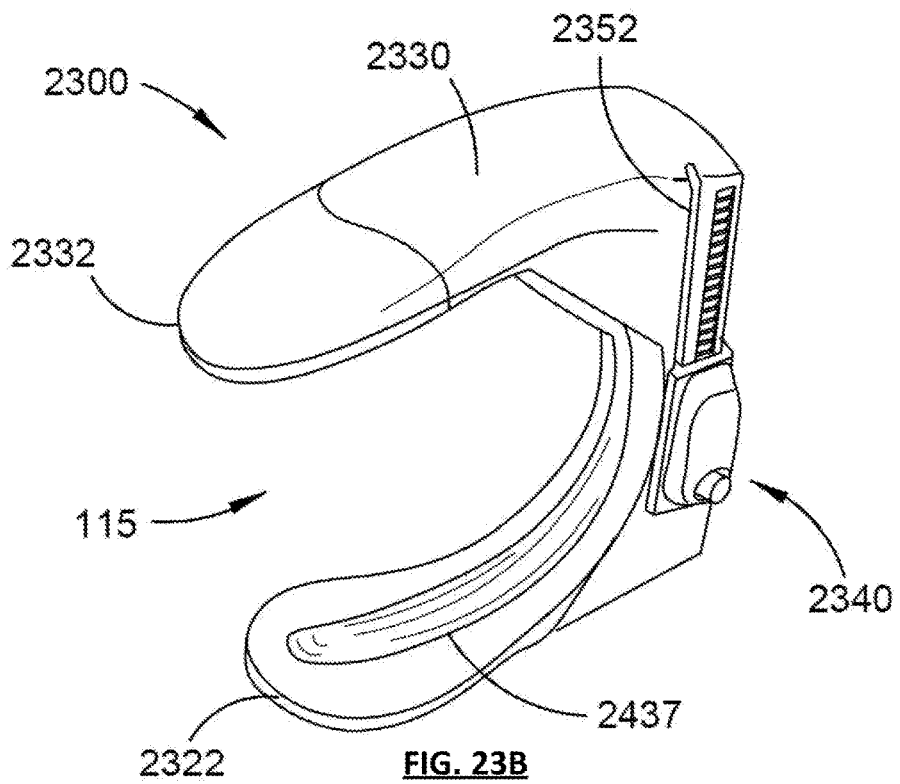
FIG. 23B is a perspective view of the clamping device of FIG. 23A but shown in an inverted position.

Referring now to FIGS. 23A and 23B, a further example clamping device 2300 is illustrated. Clamping device 2300 is similar to clamping devices 100, 600, 900, 1200, 1300 and 2100 in that it has first and second opposed jaws 2320, 2330 that are slidably movable relative to each other from an unclamped position into a clamped position and coupled to each other by a bridge portion 2310, with a retention mechanism 2340 to releasably retain the clamping device 2300 in the clamped position. Clamping device 2300 has a cushioning element 2360 extending around the U-shaped inner profile of the first and second jaws 2320, 2330 and terminating in a tongue portion 2362 near an end portion 2332 of the second jaw 2330. The tongue portion 2362 is movable along with other parts of the cushioning element 2360 adjacent the second jaw 2330 when the clamping device 2300 moves toward a clamped position. Device 2300 differs from device 100 and other device embodiments that rely on linear relative movement of the jaws in that the second jaw 2330 defines a chamber 2376 toward its end portion 2332 for progressively receiving the tongue portion 2362 as it extends during movement of the first and second jaws 2320, 2330 toward a clamped position. Thus, device 2300 does not project the tongue portion 2362 toward an external surface of the second jaw, unlike some other described embodiments.

Figures 24, 25:
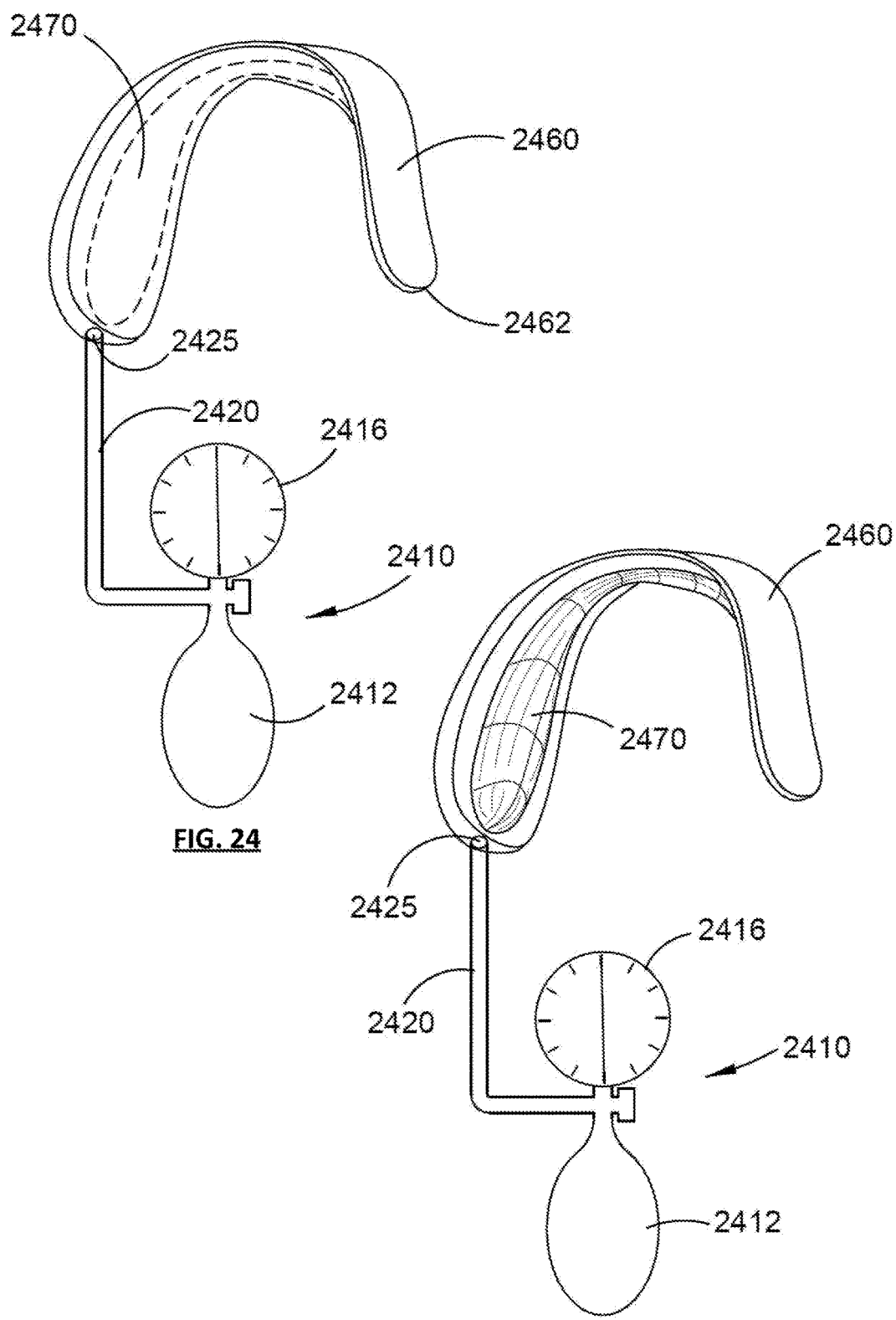
FIG. 24 is a schematic illustration of an example expandable element usable in example clamping devices.
FIG. 25 is a schematic illustration of the expandable element of FIG. 24, illustrating the expandable element in an expanded state.
Figure 26:
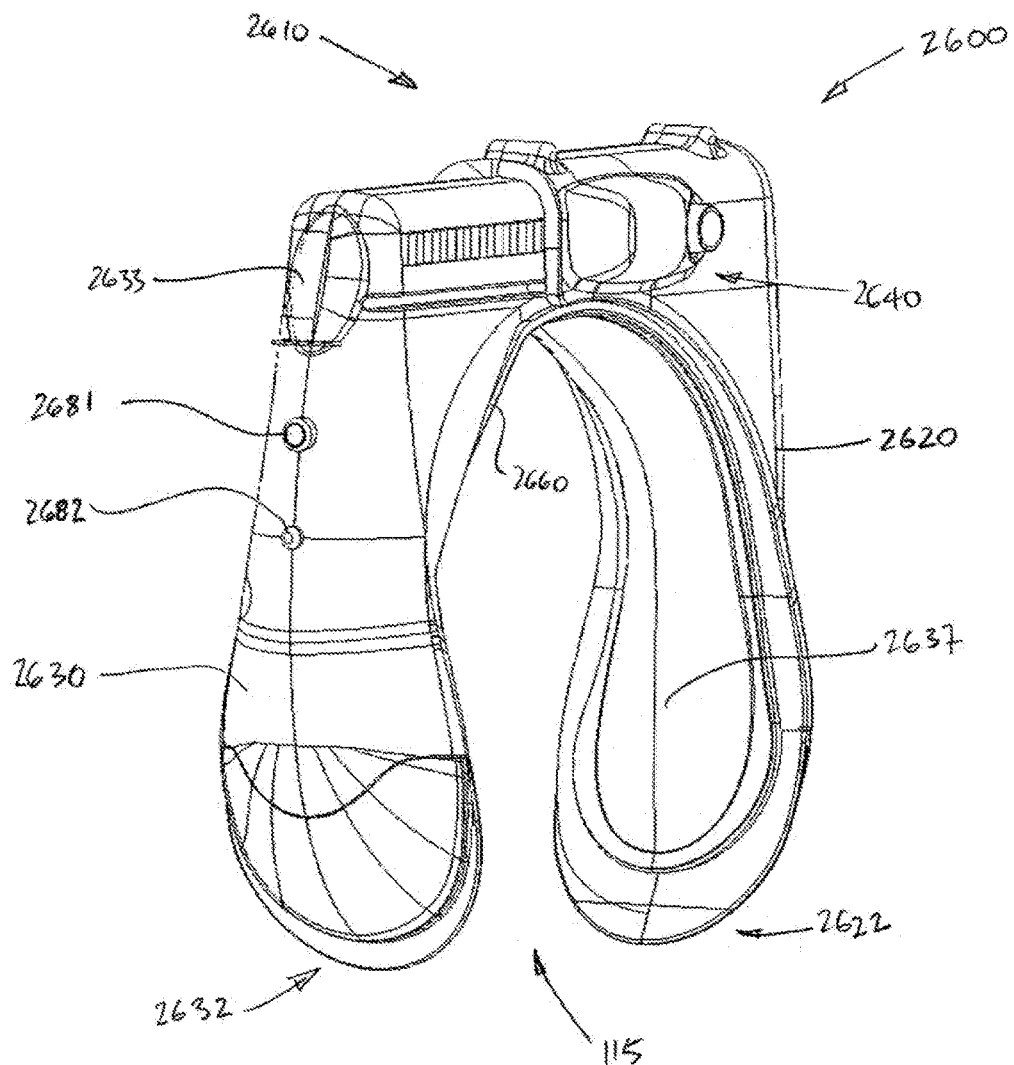
FIG. 26 is a perspective view of a clamping device according to further embodiments.
Figure 27:
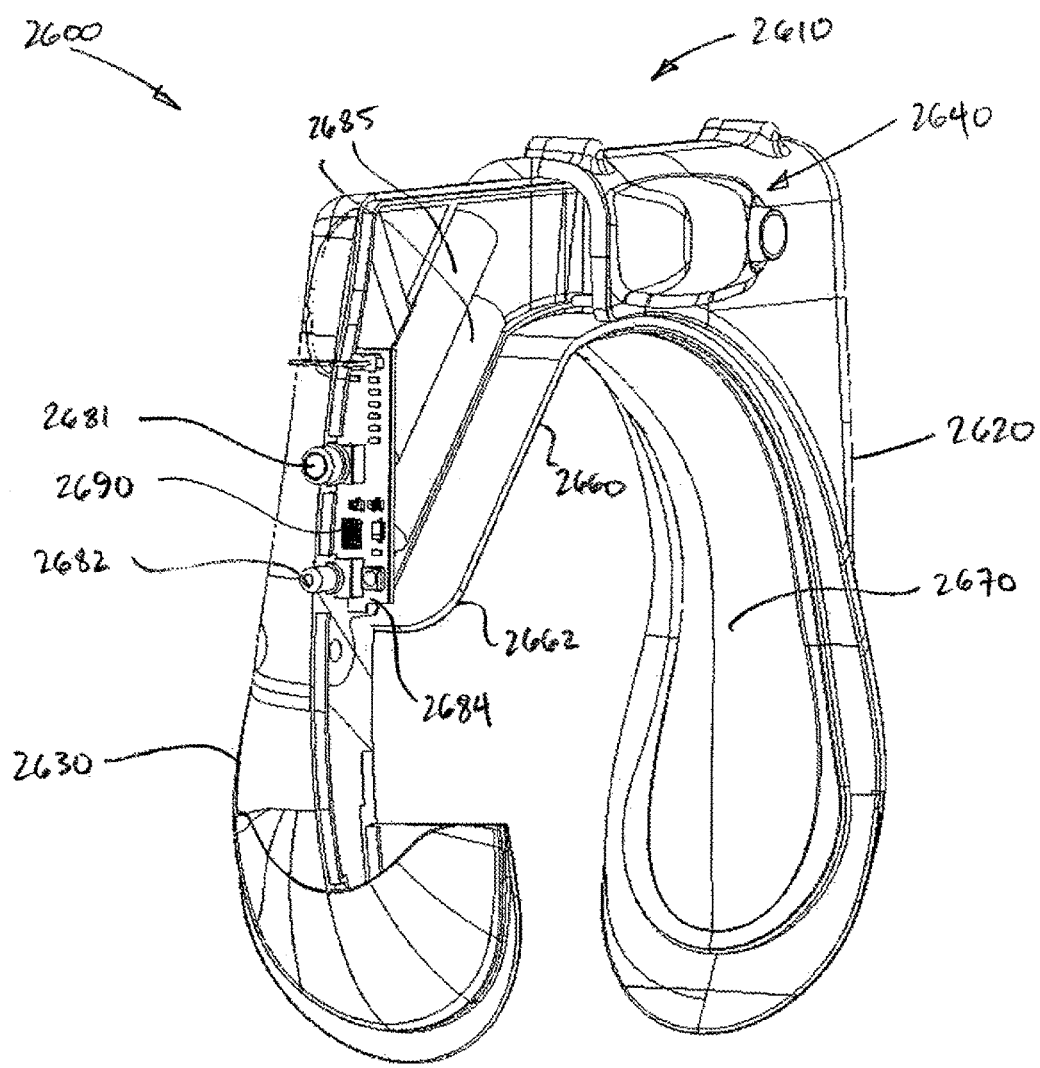
FIG. 27 is a perspective partial cut-away view of the clamping device of FIG. 26.
Figure 28:
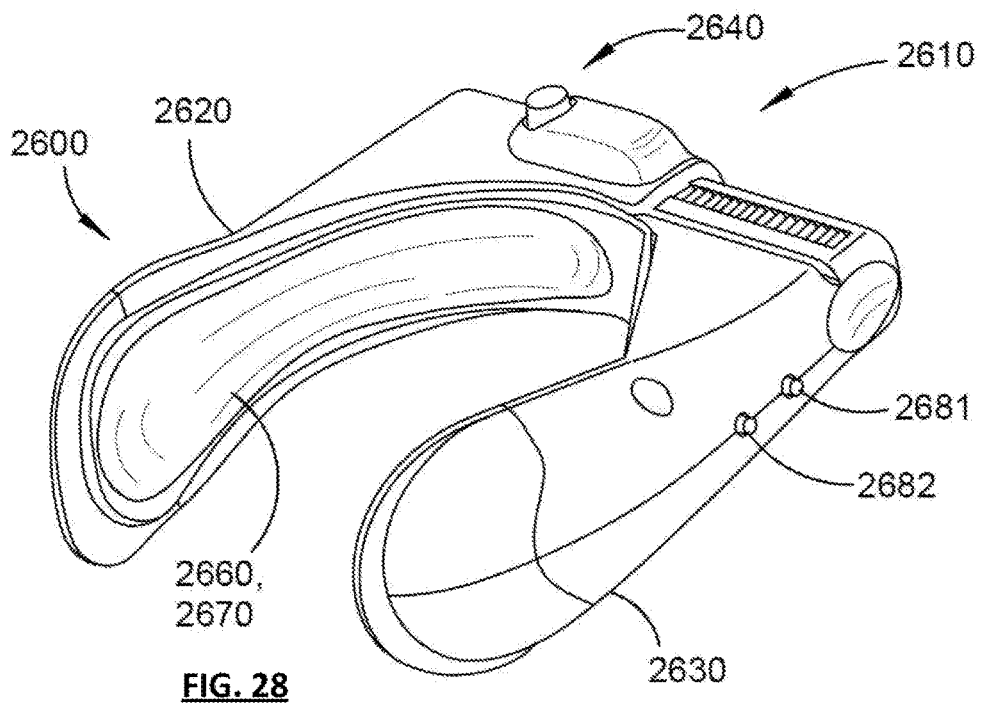
FIG. 28 is a further perspective view of the clamping device of FIG. 26.
Figure 29:
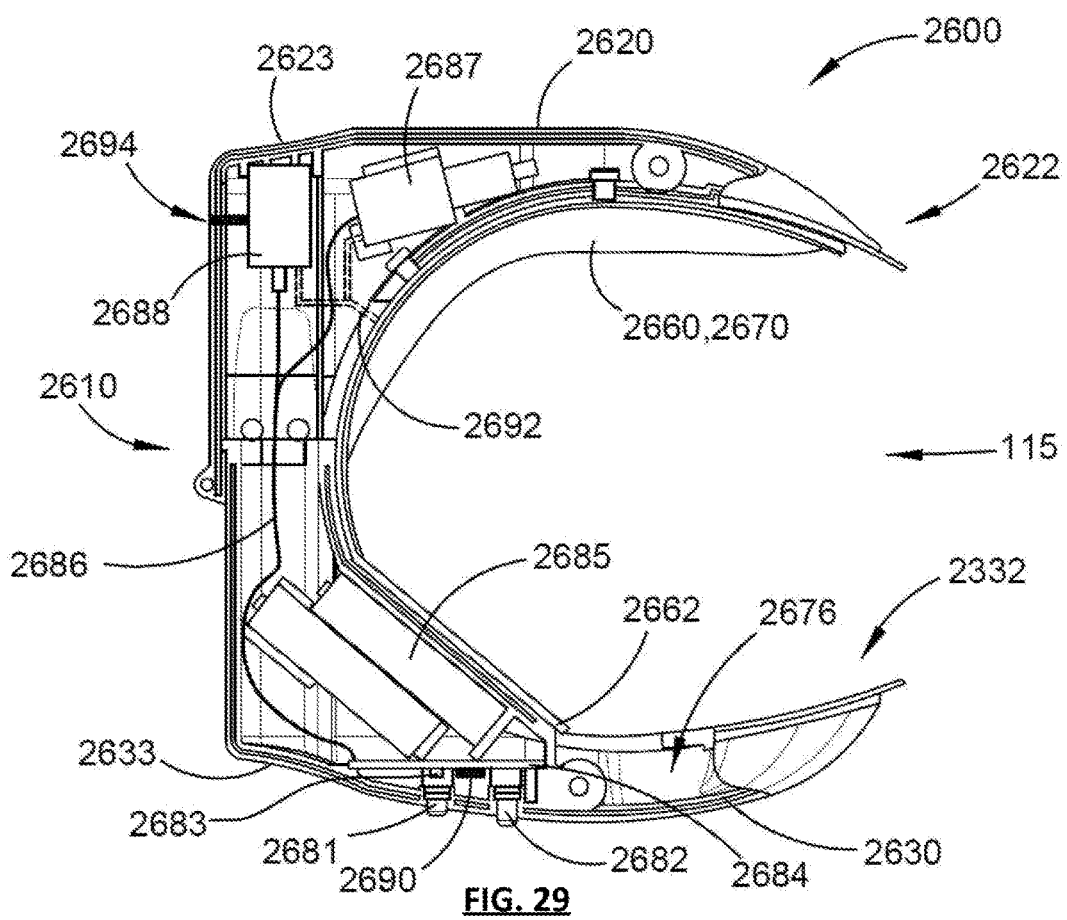
FIG. 29 is a cross-sectional view of the clamping device of FIG. 28.

Referring now to FIGS. 24 and 25, an example expandable element is schematically illustrated in conjunction with a sphygmomanometer 2410, although other forms of blood pressure meter may be employed.

As shown in FIGS. 24 and 25, an expandable element 2470 may form part of a modified cushioning element 2460 similar to the example cushioning elements previously described, but with an inflatable part in the form of expandable element 2470. The expandable element 2470 may be formed as an inflatable portion of the cushioning element 2460, with the inflatable portion being defined by a bladder at least partially received within a substantial lengthwise part of the cushioning element 2460. Alternatively, the expandable element 2470 may be formed as a separate part from the cushioning element 2460, even though the expandable element 2470 may be co-located and at least partially co-extensive therewith.

The expandable element 2470 can be used to couple with the sphygmomanometer 2410, for example via a suitable coupling valve 2425 at an exposed end of the cushioning element 2460 (for example at the end portion 2322 of the first jaw 2320 shown in FIGS. 23A and 23B). The sphygmomanometer 2410 may be an existing device, for example including a hand actuable pump 2412, a pressure indicator 2416 and a fluid conduit 2420 to pump air into and release air from the expandable element 2470 via the valve 2425. Instead of the sphygmomanometer 2410, other suitable automated or hand actuable devices may be used to pump air into and release air from the inflatable bladder of expandable element 2470.

The expandable element 2470 may form part of a core of the cushioning element 2460 and may extend at least partially along the longitudinal axis of the cushioning element 2460, optionally all the way to the tongue portion 2462 at the end of the cushioning element 2460, but possibly extending only in the order of a ½ to ⅘ of the length of the cushioning element 2460. Advantageously, the pressure applied by the expandable element 2470 may be measured by the pressure sensor shown and described above in relation to FIGS. 21 and 22.

Referring now to FIGS. 26 to 29, a further example clamping device 2600 is illustrated. Clamping device 2600 is similar to clamping devices 100, 600, 900, 1200, 1300, 2100 and 2300 in that it has first and second opposed parts (jaws/arms) 2620, 2630 that are slidably movable relative to each other from an unclamped position into a clamped position and coupled to each other by a bridge portion 2610, with a retention mechanism 2640 to releasably retain the clamping device 2600 in the clamped position.

Clamping device 2600 has a cushioning element 2660 extending around the U-shaped inner profile of the first and second jaws 2620, 2630 and terminating in a tongue portion 2662 near an end portion 2632 of the second jaw 2630. The tongue portion 2662 is movable along with other parts of the cushioning element 2660 adjacent the second jaw 2630 when the clamping device 2600 moves toward a clamped position. Device 2600 is similar to device 2300 and differs from device 100 and other device embodiments that rely on linear relative movement of the jaws in that the second jaw 2630 defines a chamber 2676 (FIG. 29) toward its end portion 2632 for progressively receiving the tongue portion 2662 as it extends during movement of the first and second jaws 2620, 2630 toward a clamped position. Thus, like device 2300, device 2600 does not project the tongue portion 2662 toward an external surface of the second jaw.

Additionally, device 2600 has an expandable element 2670 within, under or co-located with the cushioning element 2660, and may be similar to the expandable element 2470 shown and described in relation to FIGS. 24 and 25. The expandable element 2670 may comprise an inflatable bladder, for example, to assist with applying additional pressure to at least part of an arm when used to clamp the arm.

Device 2600 further comprises control functions to automate the inflation and deflation of the expandable element 2670. Such control functions may be provided by a controller 2690 on a circuit board 2684 that is electrically coupled to a pump 2687 to operate the pump 2687 to pump air into (inflate) the expandable element 2670.

The controller 2690 is also electrically coupled to a pressure relief valve 2688 (for example in the form of a small solenoid valve) to control operation of the pressure relief valve 2688 and thereby selectively allow deflation of the expandable element 2670. The controller 2690 may control operation of the pressure relief valve 2688 to selectively allow progressive and/or staged deflation of the expandable element 2670, for example in a set or programmed manner that allows blood pressure measurements to be taken using the pressure sensor 2110. The pump 2687 may be positioned inside either the first part 2620 or the second part 2630, although in the illustrated embodiment, the pump is disposed in the first part 2620. A suitable air inlet 2694 may be provided in an external wall of the part of the device 2600 within which the pump 2687 is housed. The air inlet 2694 may also function as an air outlet during deflation or there may be a separate air outlet provided in an external wall of the device 2600.

Manually actuable input components may be positioned on an outside of one of the first part 2620 and the second part 2630 and can be used to provide user control input to the controller 2690, for example via inflation and deflation actuators 2681 and 2682. The inflation actuator 2681, which may be formed as a button, and a deflation actuator 2682, which may be formed as a deflation button, may be coupled to the circuit board 2684 and may be arranged to interact with the controller 2690 to cause the controller 2690 to send control signals via separate electrical conductors (wires) 2686 to the pump 2687 and the pressure relief valve 2688, respectively, to cause inflation or deflation of the expandable element 2670.

The inflation and deflation actuators 2681, 2682 may be positioned close to each other on an external (outwardly facing) wall of the second part 2630, in between a land 2633 (for applying manual force to bring the device 2600 toward a clamped position) and a distal end 2632 of the second part 2630, as is shown in the Figures. Alternatively, the inflation and deflation actuators 2681, 2682 may be positioned close to each other on an external (outwardly facing) wall of the first part 2620, in between a land 2623 (for applying manual force to bring the device 2600 toward a clamped position) and a distal end 2622 of the first part 2630. In either case, it is preferred that the inflation and deflation actuators 2681, 2682 are positioned on a part of the device 2600 that is away from the bridge portion 2610. In a further alternative, the inflation and deflation actuators 2681, 2682 may be positioned on a part of the bridge portion 2610 that does not interfere with relative movement between the first and second parts 2620, 2630 and does not interfere with the clamping or unclamping functions of the device 2600.

Inflation of the expandable element 2670 by the pump may be controlled to achieve an internal pressure of the expandable element at a first pressure set-point or at a second pressure set-point that is higher than the first set-point. The first pressure set-point may be a pressure from about 40 mm Hg to about 80 mm Hg, and optionally about 60-70 mm Hg. The second pressure set-point may be a pressure from about 80 mm Hg to about 200 mm Hg, and optionally about 90-100 mm Hg.

The pressure relief valve 2688 may be in communication with an air inlet/outlet 2694 in an external wall of the first part 2620 (for embodiments where the pressure relief valve 2688 and the pump 2687 are in the first part 2620). The pump 2687 may in some embodiments be in fluid communication with a separate air inlet/outlet (not shown) to inlet/outlet 2694. Small tubing 2692 may be provided inside the device housing to pneumatically couple the pump 2687, the expandable element 2670 and the relief valve 2688 so that air can be pumped into the expandable element 2670 and released therefrom via the relief valve 2688.

Optionally, one or more indicators or coloured lights, such as light emitting diodes 2683, may also be provided on (or otherwise coupled to) the circuit board 2684 and may be associated with each of the actuators 2681, 2682. When one of the actuators 2681, 2682 has been manually actuated, the controller 2690 may cause one or more of the LEDs 2683 to light up to visually indicate that inflation or deflation is occurring or is about to occur or to indicate a particular status of operation of the device 2600. In some embodiments (described below) where the inflation or deflation can be effected automatically through voice commands or externally originating control commands, the LEDs 2683 may be used to indicate the operational status (e.g. mid-level inflation, maximum level inflation, deflation or progressive (staged) deflation) of the expandable element 2670.

One or more batteries 2685 housed within the second part 2630 may provide power for the controller 2690, the circuit board 2684, the LEDs 2683, the pump 2687, the relief valve 2688, plus any other external communication function, such as an audible alarm or a wireless communication function. Although not shown, terminals of the one or more batteries 2685 are electrically coupled to the circuit board 2684 to provide a power source for the circuit board 2684. The other powered components, such as the LEDs 2683, relief valve 2688, pump 2687 and controller 2690, may receive power from the one or more batteries 2685 directly or via the circuit board 2684.

Figure 30:
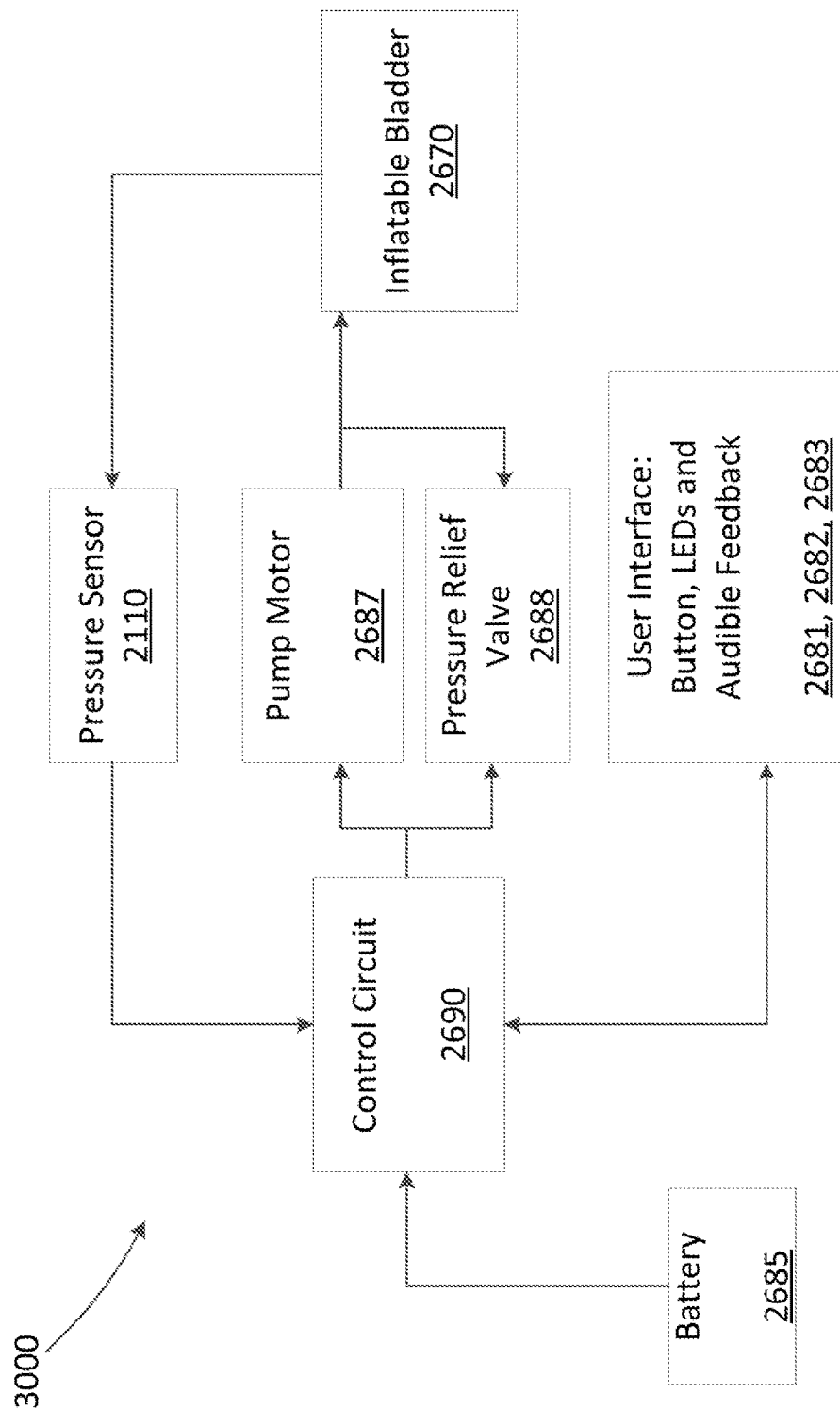
FIG. 30 is a schematic block diagram of components of the clamping device of FIG. 26.

Optionally, the pressure sensor 2110 may be used to sense the pressure in the expandable element 2670 and to provide an output signal to the controller 2690 indicative of the sensed pressure. Alternatively, the pump 2687 may have a pressure sensing function and may provide an output signal to the controller 2690 indicative of the sensed pressure in the expandable element 2670. With such signals providing feedback, the controller 2690 can relatively accurately cause the expandable element 2670 to reach the desired pressure set-point. FIG. 30 is a schematic block diagram of a clamping device 3000 having the features and functions of the clamping device 2600 described above, plus the pressure sensor 2110 (or an equivalent sensor provided by the pump 2687).

Figure 31:
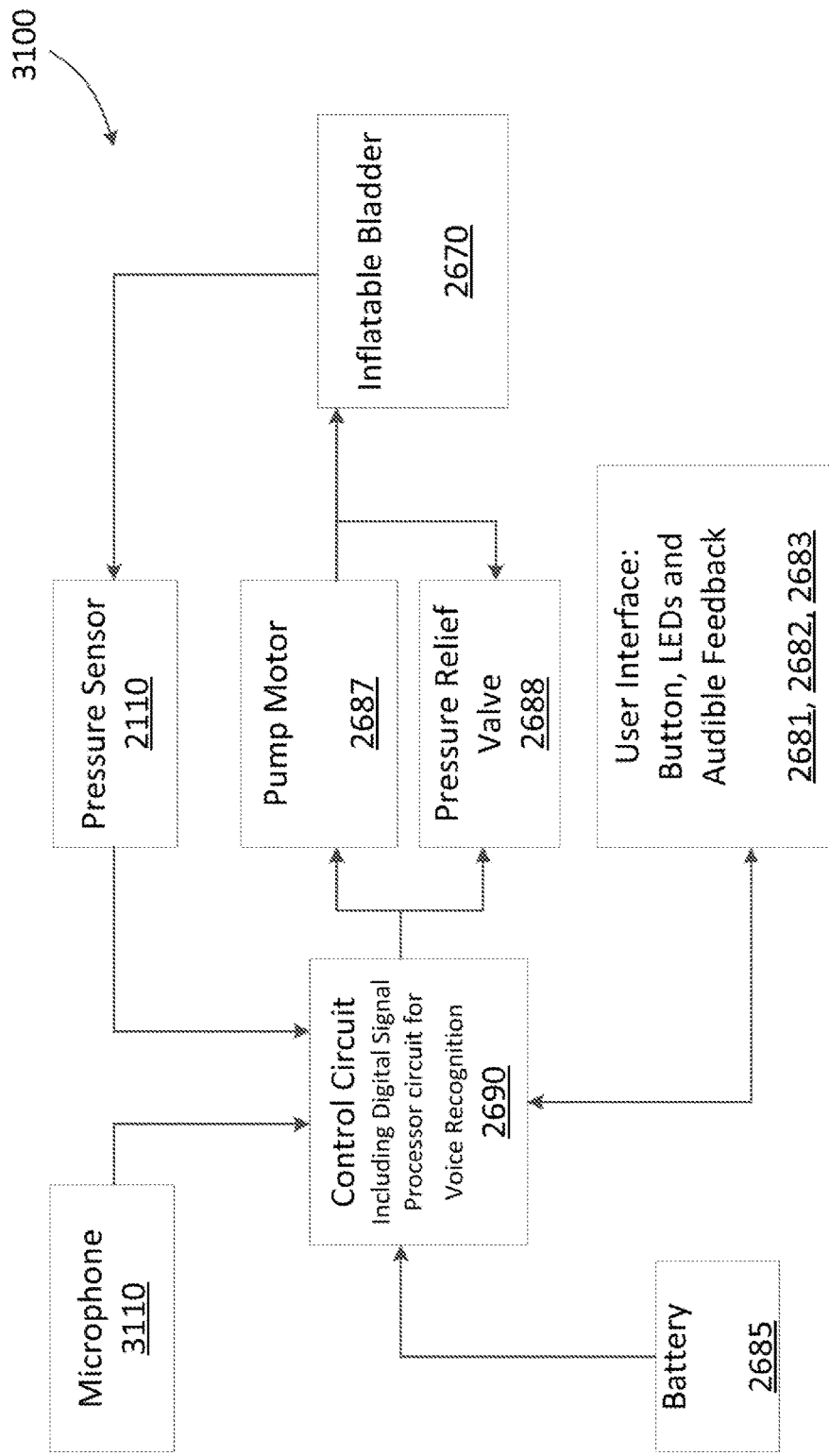
FIG. 31 is a schematic block diagram of components of a clamping device similar to FIG. 26 but including voice control features.

In some embodiments, a voice activation function may be provided to allow the inflation or deflation of the clamping device 2600 to be effected by voice commands. In such embodiments, schematically represented as device 3100 in FIG. 31, the device 2600 described above may be supplemented with an audio input component 3110, such as a microphone, and a digital signal processor (DSP) as part of the controller 2690. The controller 2690 in such embodiments may comprise suitable hardware and execute suitable software to process speech signals received via the audio input component 3110 to determine whether a valid voice command has been received. If a valid voice command is determined by the controller 2690 to have been received, then the controller 2690 operates the pump 2687 for inflation or the pressure relief valve 2688 for deflation (as appropriate) in response to the valid voice command. A trigger phrase may be used to prime the receipt of a following voice command. For example, the trigger phrase may be "command", followed by an actual voice command, such as "deflate" or "inflate". If no valid voice command is determined to have been received, no action is taken by the controller 2690.

Figure 32:
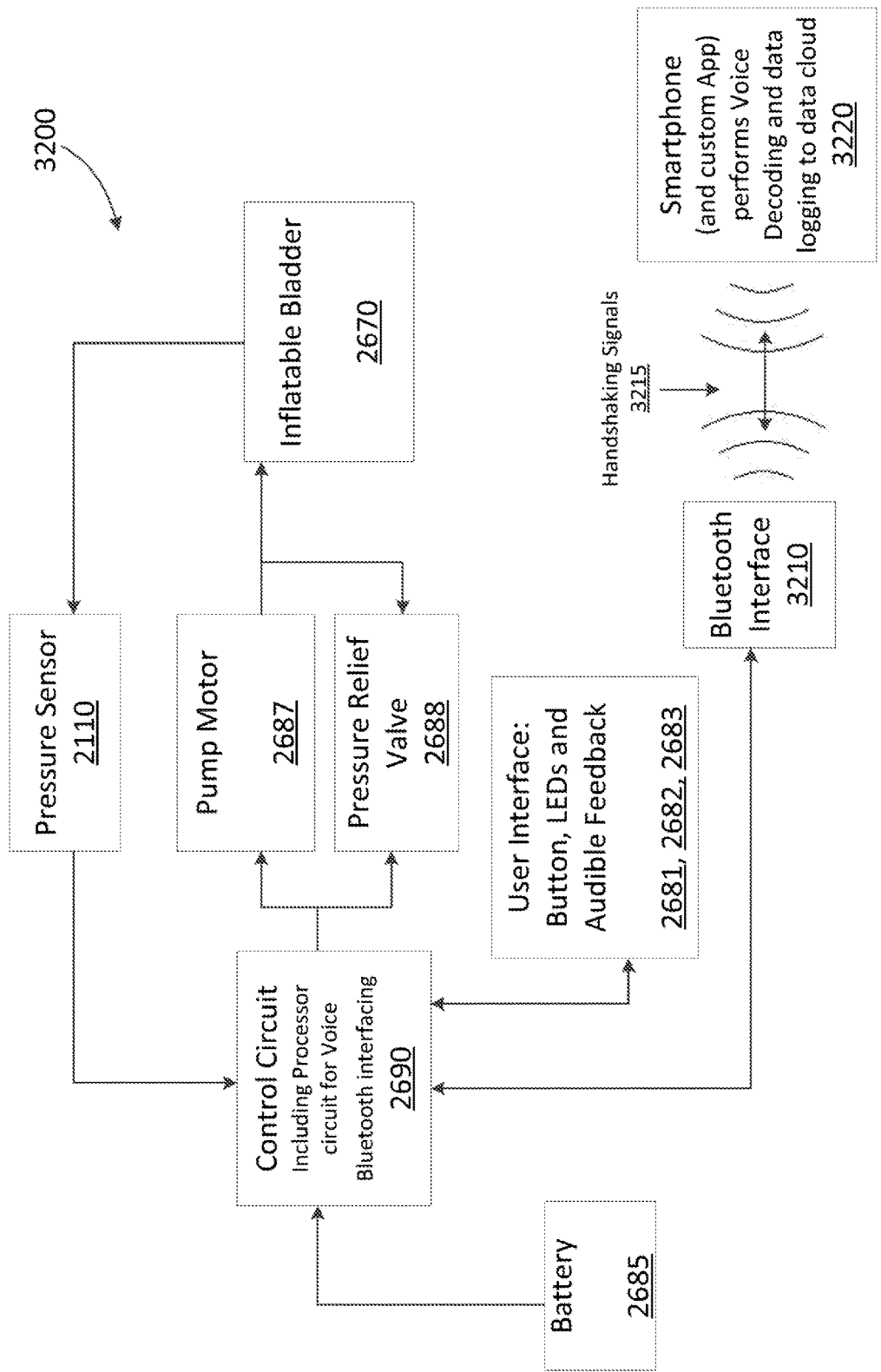
FIG. 32 is a schematic block diagram of components of a clamping device similar to FIG. 26 but including features to allow control of the clamping device by a handheld electronic device.

In some embodiments, a remote device control function may be provided to allow the inflation or deflation of the clamping device 2600 to be effected by use of an external control device. In such embodiments, schematically represented as device 3200 in FIG. 32, the device 2600 described above may be supplemented with a wireless communication module 3210, such as a short-range communications subsystem, and a digital signal processor (DSP) or other communication interface component as part of the controller 2690. The short-range communication subsystem may use a Zigbee protocol, a Bluetooth protocol, a personal area network protocol, a Wi-Fi protocol, an IEEE 802.11-compliant protocol or another suitable low-power, short range wireless communications protocol.

The controller 2690 in such embodiments may comprise suitable hardware and execute suitable software to process control commands received via the wireless communication module 3210. If a valid command is determined by the controller 2690 to have been received via the wireless communication module 3210, then the controller 2690 operates the pump 2687 or the pressure relief valve 2688 (as appropriate) in response to the valid command. If no valid command is determined to have been received, no action is taken by the controller 2690. The commands may be received at the wireless communication module 3210 from an external control device, such as a handheld computing device 3220 (for example, a smart phone or a laptop or tablet computer). Such commands may be received at the wireless communication module 3210 following exchange of handshaking signals 3215 between the wireless communication module 3210 and the handheld computing device 3220. The handheld computing device 3220 may execute an application (i.e. an "App") specifically designed to interface with the clamping device 3200 and for this purpose, the controller

2690 may be configured to send data back to the handheld computing device 3220 via the wireless communication module 3210. Such data may include sensed pressure data, device status data or other device operational data, such as power level of the batteries, component malfunctions detected (if any), number of uses of the device 3200 since a last reset (to determine when it should be cleaned next), etc. Although not shown, some embodiments may include a sensor to indicate to the controller 2690 when the device 2600/3200 has been placed in a clamped position or an unclamped position.

Some device embodiments may be suitably described as a non-encircling tourniquet, which may be implemented with two opposing movable plates. The plates may be connected via a telescoping, lockable bridge section, which allows for relative movement in a direction largely perpendicular to a common plane of the plates. The plates, bridge and locking mechanism thus effectively combine to form a clamping device. The plates are preferably shaped in such a fashion they provide specific structure to assist in compressing the veins of the (upper) arms. In this regard, the structure of the plates may be configured to provide pressure points that correlate to the location of the major veins in the arms. Such structures are strategically placed on the inside or arm side of the clamping device to achieve venous compression and at least partial venous stasis. These pressure points result in needing less pressure provided by the operator of the device, prior to venepuncture.

Embodiments may also employ a sliding sleeve or insert originating from the medial inner plate that extends along the inside of the plates and bridge, comprising a 3-4 mm raised central longitudinal spine aiding in venous compression. The sleeve or insert may protrude through the distal end of the lateral plate. Upon closing or tightening the device into a clamped position, the sleeve will protrude further through the distal lateral plate and the amount of protrusion is largely proportional to the tightening movement. This protrusion and movement is in reaction to the decreasing inner circumference of the clamping device at the bridge and aides in avoiding or minimising pinching, grabbing or injuring the skin of the arm on to which the clamping device is applied. A side button release mechanism may be provided for easy detachment.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A device for reducing venous blood flow in a human limb, the device comprising:
   a first rigid part having a first non-linear inner profile;
   a second rigid part having a second inner profile generally facing the first inner profile; and
   a coupling portion that couples the first and second rigid parts together while allowing relative movement of the first and second rigid parts between a clamped position and an unclamped position;
   wherein the first and second inner profiles are configured to press against veins in the limb when the device is in the clamped position and thereby reduce venous blood flow in the limb;
   wherein the device further comprises a cushioning element disposed on at least one of the first inner profile and the second inner profile, wherein the cushioning element extends over the first inner profile and the second inner profile, is affixed to the first inner profile and is not affixed to the second inner profile.

2. The device of claim 1, wherein the second inner profile is partly straight and partly curved.

3. The device of claim 1, further comprising at least one releasable retention mechanism to retain the device in the clamped position; wherein the at least one retention mechanism is configured to allow the device to adopt one of a plurality of retention positions in which the coupling portion is restrained from adopting the unclamped position.

4. The device of claim 1, wherein the second rigid part is partially received within a receiving portion of the first rigid part wherein, as the device is moved toward the clamped position, progressively more of the second rigid part is received within the receiving portion of the first rigid part.

5. The device of claim 1, wherein the first and second rigid parts are sized and shaped so that, when the device is in the clamped position, the first and second rigid parts do not necessarily contact the entire periphery of the limb.

6. The device of claim 1, wherein the first and second rigid parts are sized and shaped to provide only partial encirclement of the limb when the device is in the clamped position.

7. The device of claim 6, wherein the first and second rigid parts are sized and shaped to provide partial encirclement of the limb in a range of about 240° to about 300° when the device is in the clamped position.

8. The device of claim 1, further comprising a ridge defined by at least one of the cushioning element and the second inner profile, the ridge extending along at least part of a length of the cushioning element and configured to impinge on the limb when the device is in the clamped position.

9. The device of claim 1, wherein the first rigid part, the second rigid part and the coupling portion define a shape of the device that is substantially U-shaped.

10. The device of claim 1, further comprising at least one pressure sensor.

11. The device of claim 10, wherein the at least one pressure sensor is positioned in the device so that, in use of the device on an arm, the at least one pressure sensor lies adjacent a medial part of the arm.

12. The device of claim 10, further comprising an indicator coupled to the at least one pressure sensor to visibly indicate a sensed pressure.

13. The device of claim 10, wherein the at least one pressure sensor is arranged to sense a pressure applied at least in part by an expandable element.

14. The device of claim 1, further comprising an expandable element arranged at least partly along at least one of the first inner profile and the second inner profile or at least one of the inner faces of the first and second jaws.

15. The device of claim 14, wherein the expandable element is inflatable to apply pressure to the limb when the device is positioned on the limb.

16. The device of claim 14, wherein the expandable element forms part of or is at least partially enclosed by a cushioning element disposed along at least one of the first and second inner profiles or at least one of the inner faces of the first and second jaws.

17. The device of claim 14, further comprising a pump to inflate the expandable element; wherein the pump is disposed inside one of the first rigid part and the second rigid part.

18. The device of claim 17, further comprising a controller arranged to operate the pump and a power source to power the controller and the pump.

19. The device of claim 18, further comprising at least one manually actuatable input component on an outside of one of the first rigid part and the second rigid part to provide actuation input to the controller.

20. The device of claim 19, wherein the controller is configured to, in response to the actuation input, one of:
operate the pump to inflate the expandable element to a first pressure set-point;
operate the pump to inflate the expandable element to a second pressure set-point that is higher than the first set-point;
operate a pressure relief valve to deflate the expandable element; and
stop operation of the pressure relief valve.

21. The device of claim 18, further comprising a wireless communication module, wherein the controller is configured to receive a control command from an external control device via the wireless communications module and to operate the pump or a pressure relief valve in response to the control command.

22. A device for reducing venous blood flow, the device comprising:
first and second opposed jaws, each of the first and second jaws defining a rigid inner face to be pressed toward opposite sides of a limb and the first and second opposed jaws together defining a space therebetween to at least partially receive the limb, the rigid inner face of at least one of the first and second opposed jaws having a non-linear profile;
a bridge coupling the first and second opposed jaws together in a manner that allows relative movement of the first and second opposed jaws between an open position, in which the device can be positioned about at least a portion of the limb, and a clamped position, in which the rigid inner faces of the first and second opposed jaws are pressed against the opposite sides of the limb such that venous blood flow is reduced in at least superficial veins distal of the portion of the limb; and
a cushioning element disposed on at least one of the rigid inner faces,
wherein the cushioning element extends over each of the rigid inner faces, and is affixed to a first rigid inner face and not affixed to a second rigid inner face.

23. A device for reducing venous blood flow in a limb, the device comprising:
first and second opposed jaws, each of the first and second opposed jaws comprising a rigid component defining an inner face to be pressed toward opposite sides of the limb; and
a cushioning element disposed on at least one of the inner faces,
wherein the cushioning element extends over each of the inner faces and is affixed to a first inner face and not affixed to a second inner face;
wherein the first and second opposed jaws are movable between an open position, in which the device can be positioned about at least a portion of the limb, and a clamped position, in which the inner faces of the first and second opposed jaws are pressed against the opposite sides of the limb such that venous blood flow is reduced in at least superficial veins distal of the portion of the limb;
wherein the first and second opposed jaws are manually compressible from the open position to the clamped position; and
wherein the device is sized and arranged such that, when the limb is an upper arm and the device is placed in the clamped position about the upper arm with one of the first and second opposed jaws pressing against a medial side of the upper arm, the other of the first and second opposed jaws presses against an upper lateral part of the upper arm to compress the cephalic vein.

* * * * *